(12) United States Patent
Hart et al.

(10) Patent No.: US 11,793,756 B2
(45) Date of Patent: Oct. 24, 2023

(54) ANIONIC NANOCOMPLEXES FOR NUCLEIC ACID DELIVERY

(71) Applicant: UCL Business PLC, London (GB)

(72) Inventors: Stephen Hart, London (GB); Aristides Tagalakis, London (GB)

(73) Assignee: UCL Business PLC, Greater London (GB)

( * ) Notice: Subject to any disclaimer, the term of this patent is extended or adjusted under 35 U.S.C. 154(b) by 243 days.

(21) Appl. No.: 16/961,188

(22) PCT Filed: Jan. 10, 2019

(86) PCT No.: PCT/GB2019/050066
§ 371 (c)(1),
(2) Date: Jul. 9, 2020

(87) PCT Pub. No.: WO2019/138235
PCT Pub. Date: Jul. 18, 2019

(65) Prior Publication Data
US 2021/0052496 A1 Feb. 25, 2021

(30) Foreign Application Priority Data
Jan. 10, 2018 (GB) ..................... 1800370

(51) Int. Cl.
*A61K 9/127* (2006.01)
*A61P 35/00* (2006.01)
*A61K 31/7088* (2006.01)
*A61K 38/17* (2006.01)

(52) U.S. Cl.
CPC ........ *A61K 9/1271* (2013.01); *A61K 31/7088* (2013.01); *A61K 38/1709* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 2005/0025821 A1 | 2/2005 | Harvie et al. | |
| 2008/0221317 A1* | 9/2008 | Khvorova | C12N 15/111 536/24.5 |
| 2015/0246137 A1* | 9/2015 | Guo | A61K 9/127 424/649 |

FOREIGN PATENT DOCUMENTS

| | | | |
|---|---|---|---|
| WO | 9700965 | A2 | 1/1997 |
| WO | 02072616 | A2 | 9/2002 |
| WO | 2004108938 | A2 | 12/2004 |

OTHER PUBLICATIONS

Tagalakis et al (Biomaterials, 35, 8406-8415, 2014) (Year: 2014).*
International Search Report and Written Opinion issued in counterpart PCT Application No. PCT/GB2019/050066 dated May 17, 2019 (thirteen (13) pages).
Tagalakis Aristides D et al. "Multifunctional, self-assembling anionic peptide-lipid nanocomplexes for targeted siRNA delivery", Biomaterials, vol. 35, No. 29, Jun. 28, 2014 (Jun. 28, 2014), p. 8406-8415.
Kenny Gavin D et al. "Multifunctional receptor-targeted nanocomplexes for the delivery of therapeutic nucleic acids to the Brain", Biomaterials, vol. 34, No. 36, Aug. 12, 2013 (Aug. 12, 2013), p. 9190-9200.
Aryani Arian et al. "Exosomes as a Nanodelivery System: a Key to the Future of Neuromedicine?", Dec. 15, 2014 (Dec. 15, 2014), vol. 53, No. 2, p. 818-834.
GB Search Report issued in counterpart GB Application No. GB 1800370.7 dated Oct. 3, 2018 (five (5) pages).
Huang X. et al. 2016. "Preparation of Targeted Anionic Lipid-Coated Polyplexes for MicroRNA Delivery". Non-Viral Gene Delivery Vectors: Methods and Protocols, vol. 1445, pp. 201-213.
Zeng X. et al. 2015. "Surface coating of siRNApeptidomimetic nano-self-assemblies with anionic lipid bilayers enhanced gene silencing and reduced adverse effects in vitro". Nanoscale, vol. 7 (46), pp. 19687-19698.
Hattori Y. et al. 2014. "In vivo siRNA delivery system for targeting to the liver by poly-1-glutamic acidcoated lipoplex". Results in Pharma Sciences, vol. 4, pp. 1-7.
Hattori Y. et al. 2013. "Anionic polymer-coated lipoplex for safe gene delivery into tumor by systemic injection". Journal of Drug Targeting, vol. 21(7), pp. 639-647.
Zhang W. et al. 2013. "Gene transfection efficacy and biocompatibility of polycation/DNA complexes coated with enzyme degradable PEGylated hyaluronic acid". Biomaterials, vol. 34 (27), pp. 6495-6503.
Lee R. J. et al. 1996. "Folate-targeted, anionic liposome-entrapped polylysine-condensed DNA for tumor cell-specific gene transfer". The Journal of Biological Chemistry, vol. 271 (14), pp. 8481-8487.
Schroeder, A. et al. Jan. 2010. "Lipid-based nanotherapeutics for siRNA delivery". J Intern Med. 267(1): 9-21.
Zhao, Yi, and Leaf Huang. 2014. "Lipid Nanoparticles for Gene Delivery". Adv Genet. 2014 ; 88: 13-36.
Du, Z. et al. 2014. "The role of the helper lipid on the DNA transfection efficiency of lipopolyplex formulations." Sci. Rep. vol. 4:7107.
Meng, Q.H., et al. 2013. "Inhibition of neointimal hyperplasia in a rabbit vein graft model following non-viral transfection with human iNOS cDNA". Gene Therapy, vol. 20, 979-986.

(Continued)

*Primary Examiner* — Celeste A Roney
(74) *Attorney, Agent, or Firm* — David S. Bradin; Maynard Nexsen PC

(57) ABSTRACT

A non-viral delivery complex comprising a cationic core which is a nanoparticle comprising a peptide having a polycationic nucleic acid binding component, a cleavable spacer element and a cell surface receptor binding component; a nucleic acid and optionally a cationic lipid; and an anionic liposomal coating surrounding the cationic core, said coating comprising lipids from a subject's cells. Also related formulations, uses and methods.

16 Claims, 21 Drawing Sheets

Specification includes a Sequence Listing.

(56) References Cited

OTHER PUBLICATIONS

Manunta, Maria D. I. et al. 2013. "Airway Deposition of Nebulized Gene Delivery Nanocomplexes Monitored by Radioimaging Agents". Am J Respir Cell Mol Biol vol. 49, Iss. 3, pp. 471-480.

Tagalakis, Aristides D., et al. 2011. "Integrin-targeted nanocomplexes for tumour specific delivery and therapy by systemic administration". Biomaterials 32, p. 1370-1376.

Manunta, Maria D. I. et al. 2011. "Nebulisation of Receptor-Targeted Nanocomplexes for Gene Delivery to the Airway Epithelium". PLoS One, vol. 6, Issue 10. p. 1-13.

Tagalakis A. D., et al. 2008. "A Receptor-targeted Nanocomplex Vector System Optimized for Respiratory Gene Transfer". Molecular Therapy vol. 16 No. 5, 907-915.

Jenkins et al. 2003. "Formation of LID vector complexes in water alters physicochemical properties and enhances pulmonary gene expression in vivo." Gene Therapy (2003) 10, 1026-1034.

Jenkins et al. 2000. "An integrin-targeted non-viral vector for pulmonary gene therapy". Gene Therapy (2000) 7, 393-400.

Bligh, E. G. and Dyer, W. J. 1959. "A Rapid Method of Total Lipid Extraction and Purification". Can. J. Biochem. Physiol vol. 37, No. 8, p. 911-917.

Erbacher, P. et al, Gene Therapy, 1999, 6, 138-145.

Yin H, Kanasty RL, Eltoukhy AA, Vegas AJ, Dorkin JR, Anderson DG. Non-viral vectors for gene-based therapy. Nature reviews Genetics. 2014;15:541-55.

Felgner et al., Nomenclature for Synthetic Gene Delivery Systems. Human Gene Therapy 8, 1997, 511-512.

Welser K, Campbell F, Kudsiova L, Mohammadi A, Dawson N, Hart SL, et al. Gene delivery using ternary lipopolyplexes incorporating branched cationic peptides: the role of Peptide sequence and branching. Mol Pharm. 2013;10:127-41.

Tagalakis AD, He L, Saraiva L, Gustafsson KT, Hart SL. Receptor-targeted liposome-peptide nanocomplexes for siRNA delivery. Biomaterials. 2011;32:6302-15.

Grosse SM, Tagalakis AD, Mustapa MF, Elbs M, Meng QH, Mohammadi A, et al. Tumor-specific gene transfer with receptor-mediated nanocomplexes modified by polyethylene glycol shielding and endosomally cleavable lipid and peptide linkers. FASEB J. 2010;24:2301-13.

Cunningham et al., Evaluation of a porcine model for pulmonary gene transfer using a novel synthetic vector, J. Gene Med 2002, 4, 438-46.

Pangborn, A. B.; Giardello, M. A.; Grubbs, R. H.; Rosen, R. K.; Timmers, F. J. Organometallics 1996, 15, 1518-1520.

Wong JB, Hailes HC and Tabor AB, Assymetric Synthesis of Dialkyloxy-3-alkylammonium Cationic Lipids. J. Org. Chem. 2004, 69:980-983.

Hart et al., Lipid-mediated enhancement of transfection by a nonviral integrin-targeting vector. Hum Gene Ther., 1998, 9, 575-585.

Thery et al., 2006—isolating and characterization of exosomes from cell culture supernatants and biological fluids, Current Protocols in Cell Biology.

Boussif, Otmane et al. 1995. "A versatile vector for gene and oligonucelotide transfer into cells in culture and in vivo: Polyethylenimine." Proc. Natl. Acad. Sci. vol. 92, pp. 7297-7301.

Aryani, Arian and Bernd Denecke. 2016. "Exosomes as a Nanodelivery System: a Key to the Future of Neuromedicine?" Mol Neurobiol. vol. 53, pp. 818-834.

\* cited by examiner

SEQUENCE LISTING

```
<160> NUMBER OF SEQ ID NOS: 16

<210> SEQ ID NO 1
<211> LENGTH: 4
<212> TYPE: PRT
<213> ORGANISM: Artificial Sequence
<220> FEATURE:
<223> OTHER INFORMATION: cleavable portion of the spacer element peptide
      B

<400> SEQUENCE: 1

Arg Val Arg Arg
1

<210> SEQ ID NO 2
<211> LENGTH: 9
<212> TYPE: PRT
<213> ORGANISM: Artificial Sequence
<220> FEATURE:
<223> OTHER INFORMATION: Receptor binding sequence of the cell surface
      receptor binding component C
<220> FEATURE:
<221> NAME/KEY: MISC_FEATURE
<222> LOCATION: (2)..(7)
<223> OTHER INFORMATION: The residue at each of these positions can be P
      or Q

<400> SEQUENCE: 2

Leu Pro Pro Pro Pro Pro Pro His Lys
1               5

<210> SEQ ID NO 3
<211> LENGTH: 16
<212> TYPE: PRT
<213> ORGANISM: Artificial Sequence
<220> FEATURE:
<223> OTHER INFORMATION: Oligolysine polycationic nucleic acid binding
      component

<400> SEQUENCE: 3

Lys Lys Lys Lys Lys Lys Lys Lys Lys Lys Lys Lys Lys Lys Lys Lys
1               5                   10                  15

<210> SEQ ID NO 4
<211> LENGTH: 5
<212> TYPE: PRT
<213> ORGANISM: Artificial Sequence
<220> FEATURE:
<223> OTHER INFORMATION: A linker sequence of the spacer element peptide
      B
<220> FEATURE:
<221> NAME/KEY: MOD_RES
<222> LOCATION: (1)..(1)
<223> OTHER INFORMATION: 6-amino hexanoic acid
<220> FEATURE:
<221> NAME/KEY: MOD_RES
<222> LOCATION: (3)..(3)
<223> OTHER INFORMATION: 6-amino hexanoic acid

<400> SEQUENCE: 4
```

Xaa Ser Xaa Gly Gly
1               5

<210> SEQ ID NO 5
<211> LENGTH: 5
<212> TYPE: PRT
<213> ORGANISM: Artificial Sequence
<220> FEATURE:
<223> OTHER INFORMATION: A linker sequence of the spacer element peptide
      B
<220> FEATURE:
<221> NAME/KEY: MOD_RES
<222> LOCATION: (1)..(1)
<223> OTHER INFORMATION: 6-aminohexanoic acid
<220> FEATURE:
<221> NAME/KEY: MOD_RES
<222> LOCATION: (3)..(3)
<223> OTHER INFORMATION: 6-aminohexanoic acid

<400> SEQUENCE: 5

Xaa Ser Xaa Gly Ala
1               5

<210> SEQ ID NO 6
<211> LENGTH: 6
<212> TYPE: PRT
<213> ORGANISM: Artificial Sequence
<220> FEATURE:
<223> OTHER INFORMATION: A cleavable sequence and a linker sequence in
      the spacer element peptide B

<400> SEQUENCE: 6

Arg Val Arg Arg Gly Ala
1               5

<210> SEQ ID NO 7
<211> LENGTH: 6
<212> TYPE: PRT
<213> ORGANISM: Artificial Sequence
<220> FEATURE:
<223> OTHER INFORMATION: A cleavable sequence and a linker sequence in
      the spacer element peptide B

<400> SEQUENCE: 7

Arg Val Arg Arg Gly Cys
1               5

<210> SEQ ID NO 8
<211> LENGTH: 7
<212> TYPE: PRT
<213> ORGANISM: Artificial Sequence
<220> FEATURE:
<223> OTHER INFORMATION: A cleavable sequence and a linker sequence in
      the spacer element peptide B
<220> FEATURE:
<221> NAME/KEY: MOD_RES
<222> LOCATION: (5)..(5)
<223> OTHER INFORMATION: 6-amino hexanoic acid
<220> FEATURE:
<221> NAME/KEY: MOD_RES
<222> LOCATION: (7)..(7)
<223> OTHER INFORMATION: 6-amino hexanoic acid

<400> SEQUENCE: 8

Arg Val Arg Arg Xaa Ser Xaa
1               5

<210> SEQ ID NO 9
<211> LENGTH: 9
<212> TYPE: PRT

```
<213> ORGANISM: Artificial Sequence
<220> FEATURE:
<223> OTHER INFORMATION: A cleavable sequence and a linker sequence in
      the spacer element peptide B
<220> FEATURE:
<221> NAME/KEY: MOD_RES
<222> LOCATION: (5)..(5)
<223> OTHER INFORMATION: 6-amino hexanoic acid
<220> FEATURE:
<221> NAME/KEY: MOD_RES
<222> LOCATION: (7)..(7)
<223> OTHER INFORMATION: 6-amino hexanoic acid

<400> SEQUENCE: 9

Arg Val Arg Arg Xaa Ser Xaa Gly Ala
1               5

<210> SEQ ID NO 10
<211> LENGTH: 9
<212> TYPE: PRT
<213> ORGANISM: Artificial Sequence
<220> FEATURE:
<223> OTHER INFORMATION: A cleavable sequence and a linker sequence in
      the spacer element peptide B
<220> FEATURE:
<221> NAME/KEY: MOD_RES
<222> LOCATION: (5)..(5)
<223> OTHER INFORMATION: 6-amino hexanoic acid
<220> FEATURE:
<221> NAME/KEY: MOD_RES
<222> LOCATION: (7)..(7)
<223> OTHER INFORMATION: 6-amino hexanoic acid

<400> SEQUENCE: 10

Arg Val Arg Arg Xaa Ser Xaa Gly Cys
1               5

<210> SEQ ID NO 11
<211> LENGTH: 7
<212> TYPE: PRT
<213> ORGANISM: Artificial Sequence
<220> FEATURE:
<223> OTHER INFORMATION: Component of the cell surface receptor binding
      component C

<400> SEQUENCE: 11

Tyr Gly Leu Pro His Lys Phe
1               5

<210> SEQ ID NO 12
<211> LENGTH: 10
<212> TYPE: PRT
<213> ORGANISM: Artificial Sequence
<220> FEATURE:
<223> OTHER INFORMATION: Component of the cell surface receptor binding
      component C

<400> SEQUENCE: 12

Cys Tyr Gly Leu Pro His Lys Phe Cys Gly
1               5                   10

<210> SEQ ID NO 13
<211> LENGTH: 35
<212> TYPE: PRT
<213> ORGANISM: Artificial Sequence
<220> FEATURE:
<223> OTHER INFORMATION: Peptide 35 for use in accordance with the
      invention
<220> FEATURE:
<221> NAME/KEY: MOD_RES
<222> LOCATION: (21)..(21)
```

```
<223> OTHER INFORMATION: 6-amino hexanoic acid
<220> FEATURE:
<221> NAME/KEY: MOD_RES
<222> LOCATION: (23)..(23)
<223> OTHER INFORMATION: 6-amino hexanoic acid

<400> SEQUENCE: 13

Lys Lys Lys Lys Lys Lys Lys Lys Lys Lys Lys Lys Lys Lys Lys Lys
1               5                   10                  15

Arg Val Arg Arg Xaa Ser Xaa Gly Ala Cys Tyr Gly Leu Pro His Lys
            20                  25                  30

Phe Cys Gly
        35

<210> SEQ ID NO 14
<211> LENGTH: 32
<212> TYPE: PRT
<213> ORGANISM: Artificial Sequence
<220> FEATURE:
<223> OTHER INFORMATION: Peptide 32 for use in accordance with the
      invention

<400> SEQUENCE: 14

Lys Lys Lys Lys Lys Lys Lys Lys Lys Lys Lys Lys Lys Lys Lys Lys
1               5                   10                  15

Arg Val Arg Arg Gly Ala Cys Tyr Gly Leu Pro His Lys Phe Cys Gly
            20                  25                  30

<210> SEQ ID NO 15
<211> LENGTH: 29
<212> TYPE: PRT
<213> ORGANISM: Artificial Sequence
<220> FEATURE:
<223> OTHER INFORMATION: Peptide ME27 for use in accordance with the
      invention

<400> SEQUENCE: 15

Lys Lys Lys Lys Lys Lys Lys Lys Lys Lys Lys Lys Lys Lys Lys Lys
1               5                   10                  15

Arg Val Arg Arg Gly Ala Cys Arg Gly Asp Cys Leu Gly
            20                  25

<210> SEQ ID NO 16
<211> LENGTH: 28
<212> TYPE: PRT
<213> ORGANISM: Artificial Sequence
<220> FEATURE:
<223> OTHER INFORMATION: Peptide Y for use in accordance with the
      invention

<400> SEQUENCE: 16

Lys Lys Lys Lys Lys Lys Lys Lys Lys Lys Lys Lys Lys Lys Lys Lys
1               5                   10                  15

Gly Ala Cys Tyr Gly Leu Pro His Lys Phe Cys Gly
            20                  25
```

ANIONIC NANOCOMPLEXES FOR NUCLEIC ACID DELIVERY

CROSS REFERENCE TO RELATED APPLICATIONS

This application is a 35 U.S.C. § 371 U.S. national phase entry of International Application No. PCT/GB2019/050066 filed Jan. 10, 2019, which is related to and claims priority to foreign GB Application No. 1800370.7 filed on Jan. 10, 2018; the entire disclosures of which are incorporated herein by reference.

FIELD OF THE INVENTION

The present invention relates to non-viral nanocomplexes suitable for delivery of biologically-active materials, for example, nucleic acids, proteins or small molecules, to a cell, and to the use of such complexes, for example in prophylaxis, treatment and vaccination, or in vitro laboratory research.

BACKGROUND TO THE INVENTION

Gene delivery for therapy or other purposes is well-known, particularly for the treatment of diseases such as cystic fibrosis and certain cancers. The term refers to the delivery into a cell of a gene or part of a gene to correct some deficiency or defect. In the present specification the term is used also to refer to any introduction of nucleic acid material into target cells, and includes gene vaccination and the in vitro production of commercially-useful proteins in so-called cell factories.

Cell delivery systems fall into three broad classes, namely those that involve direct injection of naked DNA or RNA, those that make use of viruses or genetically modified viruses and those that make use of non-viral delivery agents. Each has its advantages and disadvantages. Although viruses as delivery agents have the advantages of high efficiency and high cell selectivity, they have the disadvantages of toxicity, production of inflammatory responses and difficulty in dealing with large DNA fragments.

In the context of cancer treatment, it may also be appropriate to deliver a gene, or other compound, which seeks not to correct the faulty cancer cell but to kill it. Obviously, in cancer treatment, it is often especially important that the therapeutic agent is selectively targeted to the appropriate cancer cells in order to minimise harm to other tissues.

Non-viral gene delivery systems are based on the compaction of genetic material into nanometric particles by electrostatic interaction between the negatively charged phosphate backbone of DNA or RNA and cationic lipids, peptides or other polymers (Erbacher, P. et al, *Gene Therapy,* 1999, 6, 138-145). The use of non-viral transfection vectors that include lipids, as opposed to viruses, can result in lower toxicity, especially lower immunogenicity; greater safety; reduced cost, reasonably efficient targeting, and an enhanced packaging ability, e.g. the ability to deal with large fragments of nucleic acid material. Unfortunately, lower transfection efficiencies have been noted. Non-viral gene therapy vectors have been the subject of recent reviews: (Yin H, Kanasty R L, Eltoukhy A A, Vegas A J, Dorkin J R, Anderson D G. *Non-viral vectors for gene-based therapy.* Nature reviews Genetics. 2014; 15:541-55; Schroeder A, Levins C G, Cortez C, Langer R, Anderson D G. *Lipid-based nanotherapeutics for siRNA delivery.* J Intern Med. 2010; 267: 9-21; Zhao Y, Huang L. *Lipid nanoparticles for gene delivery.* Adv Genet. 2014; 88:13-36.

Known complexes for gene delivery include lipoplex for lipid based nucleic acid complexes, polyplex for peptide or polymer-based complexes and lipopolyplex for hybrid systems (Felgner et al., Human Gene Therapy 8, 1997, 511-512). As used herein, the term "LPD" is a form of lipopolyplex representing a formulation comprising a lipid, an integrin-(or other receptor-) binding peptide and DNA (or other nucleic acid). LPD complexes achieve transfection via an integrin-mediated or other receptor-mediated pathway; they do not necessarily need to have an overall positive charge so undesirable serum interaction can be reduced. The peptide component provides a nucleic acid packaging function, shielding the DNA or RNA from intracellular or extracellular degradation, endosomal or otherwise. The lipid components mediate interactions with endosomal lipid bilayers by membrane fusion or permeabilisation, reducing endosomal or lysosomal degradation and allowing trafficking of the nucleic acid cargo the cytoplasm. The peptide component can be designed to be cell-type specific or cell-surface receptor specific. For example the degree of specificity for integrin or other receptors can confer a degree of cell specificity to the LPD complex. Specificity results from the targeting to the cell-surface receptors (for example integrin receptors), and transfection efficiencies comparable to some adenoviral vectors can be achieved. (Du Z, Munye M M, Tagalakis A D, Manunta M D, Hart S L. *The role of the helper lipid on the DNA transfection efficiency of lipopolyplex formulations.* Sci. Rep. 2014; 4:7107; Welser K, Campbell F, Kudsiova L, Mohammadi A, Dawson N, Hart S L, et al. *Gene delivery using ternary lipopolyplexes incorporating branched cationic peptides: the role of Peptide sequence and branching.* Mol Pharm. 2013; 10:127-41; Meng Q H, Irvine S, Tagalakis A D, McAnulty R J, McEwan J R, Hart S L. *Inhibition of neointimal hyperplasia in a rabbit vein graft model following non-viral transfection with human iNOS cDNA.* Gene Ther. 2013; 20:979-86; Manunta M D, McAnulty R J, McDowell A, Jin J, Ridout D, Fleming J, et al. *Airway deposition of nebulized gene delivery nanocomplexes monitored by radioimaging agents.* Am J Respir Cell Mol Biol. 2013; 49:471-80; Kenny G D, Bienemann A S, Tagalakis A D, Pugh J A, Weiser K, Campbell F, et al. *Multifunctional receptor-targeted nanocomplexes for the delivery of therapeutic nucleic acids to the Brain.* Biomaterials. 2013; 34:9190-200; Tagalakis A D, He L, Saraiva L, Gustafsson K T, Hart S L. *Receptor-targeted liposome peptide nanocomplexes for siRNA delivery.* Biomaterials. 2011; 32:6302-15; Tagalakis A D, Grosse S M, Meng Q H, Mustapa M F, Kwok A, Salehi S E, et al. *Integrin-targeted nanocomplexes for tumour specific delivery and therapy by systemic administration.* Biomaterials. 2011; 32:1370-6; Manunta M D, McAnulty R J, Tagalakis A D, Bottoms S E, Campbell F, Hailes H C, et al. *Nebulisation of receptor-targeted nanocomplexes for gene delivery to the airway epithelium.* PLoS One. 2011; 6:e26768; Grosse S M, Tagalakis A D, Mustapa M F, Elbs M, Meng Q H, Mohammadi A, et al. *Tumor-specific gene transfer with receptor-mediated nanocomplexes modified by polyethylene glycol shielding and endosomally cleavable lipid and peptide linkers.* FASEB J. 2010; 24:2301-13.

Peptides that target human airway epithelial cells have been reported (WO02/072616). Peptides that target dendritic cells have been reported (WO2004/108938).

Lipid/peptide vectors transfect a range of cell lines and primary cell cultures with high efficiency and low toxicity: epithelial cells (40% efficiency), vascular smooth muscle cells (50% efficiency), endothelial cells (30% efficiency) and haematopoietic cells (10% efficiency). Furthermore, in vivo transfection of bronchial epithelium of mouse has been demonstrated (Manunta M D, McAnulty R J, Tagalakis A D, Bottoms S E, Campbell F, Hailes H C, et al. *Nebulisation of receptor-targeted nanocomplexes for gene delivery to the airway epithelium.* PLoS One. 2011; 6:e26768; Tagalakis A D, McAnulty R J, Devaney J, Bottoms S E, Wong J B, Elbs M, et al., *A receptor-targeted nanocomplex vector system optimized for respiratory gene transfer.* Mol. Ther. 2008; 16:907-15. Jenkins et al., *Formation of LID vector complexes in water alters physicochemical properties and enhances pulmonary gene expression in vivo,* Gene Therapy 2003, 10, 1026-34), rat lung (Jenkins et al., *An integrin-targeted non-viral vector for pulmonary gene therapy,* Gene Therapy 2000, 7, 393-400) and pig lung (Manunta M D, McAnulty R J, McDowell A, Jin J, Ridout D, Fleming J, et al. *Airway deposition of nebulized gene delivery nanocomplexes monitored by radioimaging agents.* Am J Respir Cell Mol Biol. 2013; 49:471-80; Cunningham et al., *Evaluation of a porcine model for pulmonary gene transfer using a novel synthetic vector,* J. Gene Med 2002, 4, 438-46) and with efficiency comparable to that of an adenoviral vector (Jenkins et al., 2000, as above).

Non-viral lipid vector formulations which complex nucleic acid with cationic lipids suffer from problems of poor tissue penetration, non-specific charge-mediated binding to cells, and interactions with serum proteins which can lead to inflammatory responses Using an anionic lipid as an alternative is appealing because it offers the possibility of lower cytotoxicity, more targeting specificity and less interaction with serum components. However, because anionic vector components and nucleic acid both have a negative charge it is difficult to make complexes comprising these two components because of inherent challenges in achieving self-assembly of the complexes.

Prior art cationic lipid nanoparticles may be referred to as LPD or LPR vectors which stands, respectively, for "liposome, polycation, DNA" and "Liposome, polycation, RNA". The present invention is based on the production of what might be called "double-layered" lipid-peptide nanoparticles consisting of a nucleic acid and cationic lipid core (which may be a conventional LPD or LPR core made of a cationic liposome, a cationic peptide and the nucleic acid of interest) and an additional anionic PEGylated liposome added which coats the core nanoparticles to form a double layered nanoparticle (for example a LPDL or LPRL nanoparticle). These anionic PEGylated nanocomplexes are stable in serum and display higher transfection efficiency than anionic nanoparticles and displayed a much greater receptor-targeted specificity compared to their cationic counterparts. This contrasts with cationic, synthetic nanoparticles where PEGylation typically reduces transfection efficiency.

The anionic lipids used to apply the final anionic coating to the nanoparticle uses naturally occurring lipids including cell membranes from white blood cells or exosomes to create anionic nanoparticles. The use of lipids from donor derived cells, exosomes or other sources such as red blood cells or platelets offer the opportunity for the development of personalised nanomedicines with specific tissue targeting properties. We have demonstrated the use of WBCs and exosome derived lipids in transfections in vitro.

It is also demonstrated in accordance with the invention that nanocomplexes of the invention show a superior ability to penetrate through mucous which makes them especially promising as agents to deliver gene therapy agents to the cells in the airways of subjects having cystic fibrosis because such individuals have abnormally high levels of mucous in their lungs.

SUMMARY OF THE INVENTION

In a first aspect, the present invention provides a non-viral delivery complex for use in treating a subject, comprising:

A, a cationic core which is a nanoparticle comprising: (i) a peptide of formula A-B—C wherein A is a polycationic nucleic acid binding component, B is a spacer element that is susceptible to cleavage within a cell, and C is a cell surface receptor binding component, (ii) a nucleic acid, and optionally (iii) a cationic lipid.

B, an anionic coating which is a liposome surrounding the cationic core and which comprises lipids previously extracted from a plasma membrane of the subject's cells (for example red blood cells) or exosomes or derivatives thereof.

In a second aspect, the present invention provides a pharmaceutical composition for treating a subject which comprises the non-viral delivery complex of the first aspect of the invention in admixture or conjunction with a pharmaceutically suitable carrier.

In a third aspect, the invention provides, a method of making a non-viral delivery complex for use in treating a subject, comprising:

A, making a cationic core which is a nanoparticle comprising: (i) a peptide of formula A-B—C wherein A is a polycationic nucleic acid binding component, B is a spacer element that is susceptible to cleavage within a cell, and C is a cell surface receptor binding component, (ii) a nucleic acid, and optionally (iii) a cationic lipid.

B, adding an anionic coating which is a liposome surrounding the cationic core and which comprises lipids previously extracted from a plasma membrane of the subject's cells (for example red blood cells) or exosomes or derivatives thereof.

In a fourth aspect, the invention provides a method for the treatment or prophylaxis of a condition caused in a subject by a defect and/or a deficiency in a gene or for therapeutic or prophylactic immunisation, or for anti-sense or RNAi therapy, which comprises administering a non-viral delivery complex of the first aspect of the invention or pharmaceutical composition of the second aspect of the invention to the subject.

In a fifth aspect, the invention provides a method for the treatment of a subject suffering from a cancer which comprises administering a non-viral delivery complex of the first aspect of the invention or pharmaceutical composition of the second aspect of the invention to subject.

In an sixth aspect, the invention provides the use a non-viral delivery complex of the first aspect of the invention or pharmaceutical composition of the second aspect of the invention for the manufacture of a medicament for the treatment or prophylaxis of cancer in the subject.

In a seventh aspect, the invention provides a non-viral delivery complex, comprising:

A, a cationic core which is a nanoparticle comprising: (i) a peptide of formula A-B—C wherein A is a polycationic nucleic acid binding component, B is a spacer element that is susceptible to cleavage within a cell, and C is a cell surface receptor binding component, (ii) a nucleic acid, and optionally (iii) a cationic lipid.

B, an anionic coating which is a liposome surrounding the cationic core and which comprises lipids previously extracted from a plasma membrane of a subject's cells (for example red blood cells) or exosomes or derivatives thereof.

In an eighth, aspect the invention provides a pharmaceutical composition comprising a non-viral delivery complex according to the seventh aspect.

DETAILED DESCRIPTION OF THE INVENTION

Figure 1:
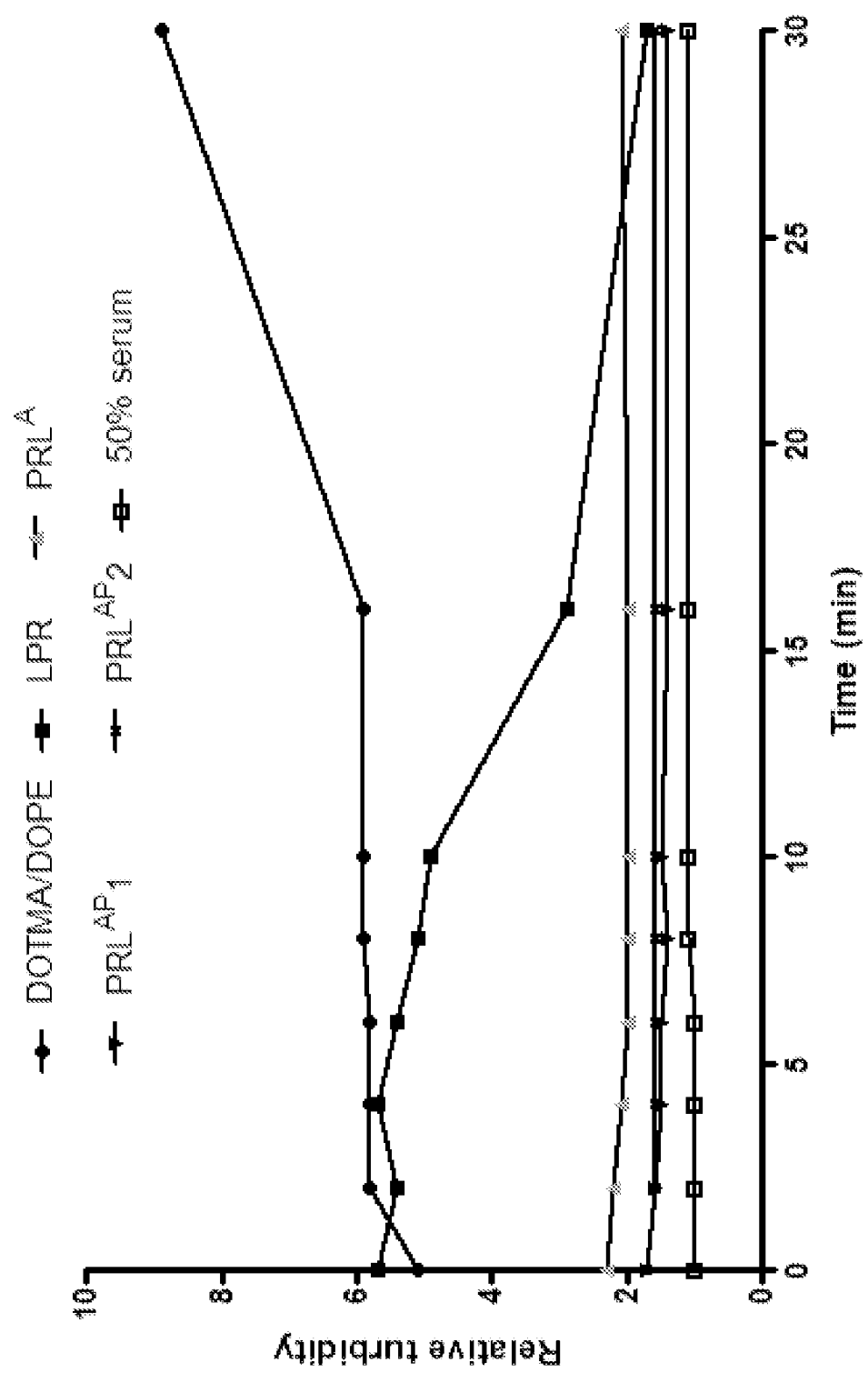
FIG. 1 shows the results of a stability comparison between non-viral delivery complexes of the invention and prior art complexes as assessed by changes in turbidity in 50% serum.

In a first aspect, the present invention provides a non-viral delivery complex for use in treating a subject, comprising:

A, a cationic core which is a nanoparticle comprising: (i) a peptide of formula A-B—C wherein A is a polycationic nucleic acid binding component, B is a spacer element that is susceptible to cleavage within a cell, and C is a cell surface receptor binding component, (ii) a nucleic acid, and optionally (iii) a cationic lipid.

B, an anionic coating which is a liposome surrounding the cationic core and which comprises lipids previously extracted from a plasma membrane of the subject's cells (for example red blood cells) or exosomes or derivatives thereof.

Preferably at least a proportion of the anionic coating consists of PEGylated lipids. Those lipids may be synthetically produced and may be introduced with PEG groups already attached into the lipid bilayer of the cationic coating. Alternatively, or additionally, they may be lipids previously extracted from a plasma membrane of the subject's cells which have had PEG groups attached to make them PEGylated derivatives.

According to certain embodiments the anionic coating is at least 50, 60, 70, 80 or 90% (by weight) previously extracted from the plasma membranes of human cells (especially cells from the subject to be treated). In some embodiments at least 50, 60, 70, 80 or 90% of the anionic coating may be extracted from the plasma membranes of human cells (especially cells from the subject to be treated) and the remaining proportion of the anionic coating consists of lipids which have been PEGylated.

Human cells may be primary human cells (for example red blood cells freshly separated from a subject) or they may be cultured human cells. Exosomes may be obtained from the blood plasma of a subject (or in some embodiments from another body fluid such as urine, saliva or breast milk) or they may be obtained from the supernatant of a cell culture. Plasma membranes may be separated from human cells or exosomes by any standard technique, for example those described in H. Evans (Ed.), Biological Membranes. A Practical Approach, IRL Press, Washington, D.C., 1987, pp. 1-35.

A suitable method of obtaining exosomes from a cell culture is described in the examples herein.

According to some embodiments, the cationic core comprises all components (i), (ii) and (iii).

According to some embodiments the ratio of cationic core A to anionic coating B is between 2 and 50, for example between 5 and 40, 5 and 30, 8 and 25 or 10 and 20. These ratios are preferably calculated on a weight basis.

In a second aspect, the present invention provides a pharmaceutical composition for treating a subject which comprises the non-viral delivery complex of the first aspect of the invention in admixture or conjunction with a pharmaceutically suitable carrier.

In a third aspect, the invention provides, a method of making a non-viral delivery complex for use in treating a subject, comprising:

A, making a cationic core which is a nanoparticle comprising: (i) a peptide of formula A-B—C wherein A is a polycationic nucleic acid binding component, B is a spacer element that is susceptible to cleavage within a cell, and C is a cell surface receptor binding component, (ii) a nucleic acid, and optionally (iii) a cationic lipid.

B, adding an anionic coating which is a liposome surrounding the cationic core and which comprises lipids previously extracted from a plasma membrane of the subject's cells (for example red blood cells) or exosomes or derivatives thereof.

Preferably at least a proportion of the lipids of the coating whether they be lipids previously extracted from a plasma membrane of the subject's cells, or lipids from another source admixed therewith are PEGylated derivatives.

According to some embodiments, the cationic core comprises all components (i), (ii) and (iii).

In a fourth aspect, the invention provides a method for the treatment or prophylaxis of a condition caused in a subject by a defect and/or a deficiency in a gene or for therapeutic or prophylactic immunisation, or for anti-sense or RNAi therapy, which comprises administering a non-viral delivery complex of the first aspect of the invention or pharmaceutical composition of the second aspect of the invention to the subject.

In a fifth aspect, the invention provides a method for the treatment of a subject suffering from a cancer which comprises administering a non-viral delivery complex of the first aspect of the invention or pharmaceutical composition of the second aspect of the invention to subject.

In an sixth aspect, the invention provides the use a non-viral delivery complex of the first aspect of the invention or pharmaceutical composition of the second aspect of the invention for the manufacture of a medicament for the treatment or prophylaxis of cancer in the subject.

In a seventh aspect, the invention provides a non-viral delivery complex, comprising:

A, a cationic core which is a nanoparticle comprising: (i) a peptide of formula A-B—C wherein A is a polycationic nucleic acid binding component, B is a spacer element that is susceptible to cleavage within a cell, and C is a cell surface receptor binding component, (ii) a nucleic acid, and optionally (iii) a cationic lipid.

B, an anionic coating which is a liposome surrounding the cationic core and which comprises lipids previously extracted from a plasma membrane of a subject's cells (for example red blood cells) or exosomes or derivatives thereof.

In an eighth, aspect the invention provides a pharmaceutical composition comprising a non-viral delivery complex according to the seventh aspect.

It is to be Understood that Features of the Invention Described with Reference to One Aspect are Also Contemplated for Use with Other Aspects of the Invention Cationic Lipids Cationic lipids are lipids with an overall positive charge under physiological conditions. Typically they are fatty acid derivatives such as triglycerides, diglycerides, monoglycerides and phospholipids. According to some embodiments of all aspects of the invention, the lipids contain an ethanolamine group which provides a positive charge.

The cationic lipid for use in accordance with the invention in all its aspects preferably comprises a cation of the formula (1):

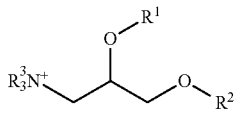

Formula (1)

in which $R^1$ and $R^2$ are each independently a $C_{10-22}$ unsaturated alkyl chain.

Advantageously, $R^1$ and $R^2$ are the same or different and are each independently a $C_{10-22}$ unsaturated alkenyl group including one or two unsaturated C=C double bonds, preferably one C=C double bond. The C=C double bonds are preferably cis-. Optionally, $R^1$ and $R^2$ are each independently a $C_{12-20}$ alkenyl group, for example, a $C_{14-18}$ alkenyl group. $R^1$ and $R^2$ optionally have straight (i.e. unbranched) alkyl chains. $R^1$ and $R^2$ may, for example, be each independently selected from $C_{12-20}$, straight chain alkenyl groups having one C=C unsaturated double bond; or $R^1$ and $R^2$ may, for example, be each independently selected from $C_{14-18}$, straight chain alkenyl groups having one cis-C=C unsaturated double bond. Optionally, $R^1$ and $R^2$ are the same or different and are each independently a straight chain, unsaturated $C_{14}$, $C_{16}$ or $C_{18}$ alkenyl group having one double bond. Optionally $R^1$ and $R^2$ are selected from —$(CH_2)_{6-12}CH$=$CH(CH_2)_{1-9}$ $CH_3$, especially —$(CH_2)_{7-11}CH$=$CH(CH_2)_{1-8}$ $CH_3$ or —$(CH_2)_{8-10}CH$=$CH(CH_2)_{1-7}$ $CH_3$, such as —$(CH_2)_{10}CH$=$CH(CH_2)_{1}CH_3$, —$(CH_2)_{8}CH$=$CH(CH_2)_{7}CH_3$ or —$(CH_2)_{10}CH$=$CH(CH_2)_{3}CH_3$. Preferably, the double bond is cis and $R^1$ and $R^2$ are selected from —$(CH_2)_{6-12}CH[Z]$=$CH(CH_2)_{1-9}CH_3$, especially —$(CH_2)_{7-11}CH[Z]$=$CH(CH_2)_{1-8}CH_3$ or —$(CH_2)_{8-10}[Z]CH$=$CH(CH_2)_{1-7}$ $CH_3$, such as —$(CH_2)_{10}[Z]CH$=$CH(CH_2)CH_3$, —$(CH_2)_{8}[Z]CH$=$CH(CH_2)_{7}CH_3$ or —$(CH_2)_{10}[Z]CH$=$CH(CH_2)_{3}CH_3$. Preferably, $R^1$ and $R^2$ are the same.

Each $R^3$ group is independently selected from hydrogen and $C_{1-4}$ alkyl. Preferably, each $R^3$ is independently selected from hydrogen or methyl. Each $R^3$ may be hydrogen or each $R^3$ may be methyl. In a preferred embodiment, each $R^3$ is methyl.

In addition to the cation, the cationic lipids may comprise a counter anion, for example, an inorganic counter ion, especially a pharmaceutically acceptable anion such as chloride or bromide.

Examples of especially suitable cations are DTDTMA (ditetradecyl trimethyl ammonium), DOTMA (2,3-dioleyloxypropyl-1-trimentyl ammonium) and DHDTMA (dihexadecyl trimethyl ammonium). Cationic lipids comprising the above cations and chloride counter anions are illustrated below:

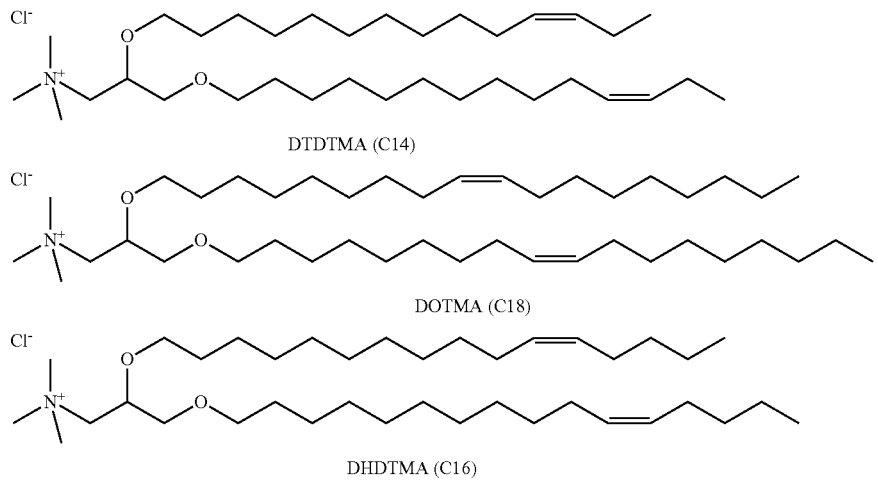

DTDTMA (C14)

DOTMA (C18)

DHDTMA (C16)

It is to be understood that the cationic lipid according to all aspects of the invention may not necessarily be the only lipid present in the cationic core. Other lipids which may be neutral, anionic or cationic may also be present. Preferably, the overall cationic lipid(s) is/are present as the most proponderant lipid in the core (on a molar ratio basis). Preferably, at least 60, 70, 80, 85 or 90% of the total lipid present in the cationic core is a cationic lipid, for example at least 60, 70, 80, 85 or 90% of the total lipid present in the cationic core may be DTDTMA, DOTMA or DHDTMA or mixtures thereof.

Peptides

The peptide for use in accordance with the invention in all its aspects is of the structure A-B—C wherein:

A is a polycationic nucleic acid-binding component,
B is a spacer element comprising the amino acid sequence RVRR (SEQ ID NO: 1), and
C is a cell surface receptor binding component comprising the amino acid sequence LX$^6$HK in which X$^6$ is Q or P (SEQ ID NO: 2).

The polycationic nucleic acid-binding component A is any polycation that is capable of binding to DNA or RNA. A polycation may be polycationic itself or it may have any number of cationic monomers provided the ability to bind to DNA or RNA is retained. For example, from 3 to 100 cationic monomers may be present, for example, from 10 to 20, for example from 14 to 18, for example, about 16.

The term "polycationic nucleic acid-binding component" is well known in the art and refers to polymers having at least 3 repeat cationic amino acid residues or other cationic unit bearing positively charged groups, such polymers being capable of complexion with a nucleic acid under physiological conditions. An example of a nucleic acid-binding polycationic molecule is an oligopeptide comprising one or more cationic amino acids. Such an oligopeptide may, for example, be an oligo-lysine molecule, an oligo-histidine molecule, an oligo-arginine molecule, an oligo-ornithine molecule, an oligo diaminopropionic acid molecule, or an oligo-diaminobutyric acid molecule, or a combined oligomer comprising or consisting of any combination of histidine, arginine, lysine, ornithine diaminopropionic acid, and diaminobutyric acid residues. Any of the above oligopeptides may have, for example, a total of from 3 to 35, for example, from 5 to 25 residues, preferably from 10 to 20 residues, for example, from 14 to 18 residues, for example 16 residues.

An oligolysine is particularly preferred, for example, having from 3 to 35, for example, from 2 to 25, for example, form 10 to 20 lysine residues, for example, from 13 to 19, for example, from 14 to 18, for example, from 15 to 17 residues, for example, 16 residues i.e. $[K]_{16}$, "K" denoting lysine (SEQ ID NO: 3).

Further examples of polycationic components include dendrimers and polyethylenimine Polyethylenimine (PEI) is a non-toxic, cross-linked cationic polymer with gene delivery potential (*Proc. Natl. Acad. Sci.,* 1995, 92, 7297-7301). Polyethylenimine is obtainable from Fluka (800 kDa) or from Sigma (50 kDa) or alternatively pre-diluted for transfection purposes from PolyPlus-tranfection (Illkirch, France). Typically, PEI is most efficient when used in a 9 fold excess over DNA, the excess ratio being calculated as PEI nitrogen:DNA phosphate, and at pH 5 to 8. Such parameters may be optimised in a manner familiar to the person skilled in the art.

The spacer element peptide B is advantageously comprises three or more amino acids, for example, four or more, for example, five or more, for example, ten amino acids or more, for example up to twelve amino acids. The spacer element may, for example, comprise from 4 to 10 amino acids, such as from 6 to 8 amino acids. The amino acids may be naturally occurring or non-naturally occurring. They may have L- or D-configuration. The amino acids may be the same or different, but the use of multiple lysine residues (or other cationic amino acids suitable for use in the polycationic nucleic acid-binding component of a vector complex) should generally be avoided in the spacer as oligo-lysine sequences have activity as a polycationic nucleic acid-binding component.

The spacer element peptide B advantageously includes a cleavable portion that is susceptible to cleavage within a cell. A spacer element peptide B that includes a cleavable portion that is susceptible to cleavage within a cell may be susceptible to cleavage within the endosome, lysosome, and/or cytoplasm of a cell. Susceptible to cleavage is understood herein to mean that the element is susceptible to cleavage over a timescale during which the components A and C remain intact. Element B is cleaved more rapidly than the cellular peptide-degradation pathways take effect. The cleavable portion typically includes from 3 to 6 amino acids, for example 4 amino acids. The spacer element B advantageously includes the amino acid sequence RVRR as a cleavable portion. The amino acid sequence RVRR is susceptible to enzymatic cleavage by the endosomal protease furin. Advantageously, the cleavable portion of the spacer element peptide B is bonded to the nucleic acid-binding component A.

The spacer element peptide B may additionally comprise a linker, which is preferably either a peptide, that is to say, it comprises amino acid residues, or a polyethyleneglycol group, or a mixture of the two. The amino acids may be naturally occurring or non-naturally occurring. They may have L- or D-configuration. The linker may have two or more amino acids. It may, for example, comprise three or more amino acids, for example, four or more, for example, five or more, for example, up to ten amino acids. The linker typically includes from 2 to 7 amino acids, for example from 3 to 5 amino acids. The amino acids may be the same or different. The linker may, for example, comprise the dipeptide glycine-glycine (GG) or glycine-alanine (GA). The linker may comprise a hydrophobic spacer. The linker may include the amino acid sequence XSX in which X is ε-aminocaproic acid (ε-Ahx) also known as 6-aminohexanoic acid, a synthetic, i.e. non-naturally occurring, amino acid Aminocaproic acid functions as a hydrophobic spacer. Examples of suitable linkers include GG, GA, XSXGG (SEQ ID NO: 4) and XSXGA (SEQ ID NO: 5). Particularly preferred linkers are XSXGA (SEQ ID NO: 5) and GA. Preferably, the linker is at the end of the spacer element peptide B which is bonded to the cell surface receptor binding component C.

The spacer element peptide B advantageously comprises a cleavable portion comprising the sequence RVRR (SEQ ID NO: 1) which is bonded to the nucleic acid-binding component A and a linker which is bonded to the cell surface receptor binding component C. The spacer element B may, for example, includes or consist of the amino acid sequence RVRR (SEQ ID NO: 1), RVRRGA (SEQ ID NO: 6), RVRRGC (SEQ ID NO: 7), RVRRXSX (SEQ ID NO: 8), RVRRXSXGA (SEQ ID NO: 9) or RVRRXSXGC (SEQ ID NO: 10), especially RVRRGA (SEQ ID NO: 6) or RVRRXSXGA (SEQ ID NO: 9).

Preferably the cell surface receptor binding component C comprises a peptide. Where cell surface receptor binding component C comprises a peptide, the peptide may be up to 20 amino acids in length, or may be longer. The peptide generally has at least 5 amino acids but may have fewer. Generally, the peptide has any number of amino acids from 6 to 20 inclusive. Generally, it is preferred for the peptide to have 15 amino acids or fewer, more preferably 12 amino acids or fewer. Generally, it is preferred for the peptide to have 5 or more amino acids, for example, 6 or more amino acids. Most preferably, the peptide has 7 to 10 amino acids.

The cell surface receptor binding component C comprises a receptor binding portion which comprises an amino acid sequence that binds to cell surface receptors. The cell surface receptor binding component C advantageously comprises a receptor binding portion which is capable of binding to human airway epithelial (HAE) cells. Examples of HAE cell-binding peptides are described in WO 02/072616. The receptor binding portion optionally comprises the amino acid sequence LX$^6$HK in which X$^6$ is Q or P (SEQ ID NO: 2). Preferably X$^6$ is P. The cell surface receptor binding component C preferably comprises the amino acid sequence YGLPHKF (SEQ ID NO: 11).

The cell surface receptor binding component C advantageously comprises a peptide comprising a cyclic region. Cyclic peptides may be formed by the provision of at least two cysteine residues in the peptide, thus enabling the formation of a disulphide bond. Accordingly, preferred cell surface receptor binding components C consist of or comprise a peptide having two or more cysteine residues that are capable of forming one or more disulphide bond(s). Preferably the cysteine residues flank the primary receptor binding portion.

The cell surface receptor binding component C optionally comprises the amino acid sequence CYGLPHKFCG (SEQ ID NO: 12).

The peptide of structure A-B—C may for example comprise a nucleic acid binding polycation, such as polylysine, bonded to RVRR (SEQ ID NO: 1), the cleavable portion of a spacer element, followed by a linker portion comprising the amino acid sequence XSXGA (SEQ ID NO: 5) or GA bonded to a cell surface receptor binding component YGLPHKF (SEQ ID NO: 11), optionally flanked by two cysteine residues.

Particular peptides suitable for use in accordance with the invention are:

```
Peptide 35:
                              (SEQ ID NO: 13)
K16-RVRR-XSXGA-CYGLPHKFCG;
and Peptide 32:
                              (SEQ ID NO: 14)
K16-RVRR-GA-CYGLPHKFCG.
```

Anionic Coating

The anionic coating according to the present invention in all its aspects is preferably a lipid bilayer liposome comprising anionic lipids. It is understood that the anionic coating does not need to comprise anionic lipids exclusively, but merely that the number of anionic lipid negative charges in the coating is greater than the number of positive charges on other lipids of the anionic coating.

In accordance with the invention the anionic coating comprises lipids previously extracted from a plasma membrane of the subject's cells, for example red blood cells or exosomes or derivatives thereof. In some embodiments lipids previously extracted from a plasma membrane of the subject's cells make up at least 50% (for example, at least 60, 70, 80 or 90%) of the lipids of the anionic coating by weight. Lipid extracted from such a source may be substantially purified or may remain mixed with other plasma membrane components (for example proteins and sugars). According to some embodiments the anionic coating is substantially (for example at least 50, 60, 70, 80 or 90%) "raw" plasma membrane as extracted from a cell or exosome. If that is the case, it will be appreciated that the non-lipid components have antigenic potential and it is therefore preferred that the cell or exosome is autologous (i.e., obtained from the individual subject to which the non-viral delivery complex is intended to be administered).

In some embodiments, the anionic coating comprises lipids previously extracted from a plasma membrane of the same cell type as that which is to be targeted by the viral delivery complex. In some embodiments, the plasma membrane may be extracted directly from the cells. In other embodiments, the cells may first be multiplied in culture before their plasma membrane is harvested. In other embodiments, the plasma membrane may be harvested from exosomes shed into a medium into which cells have been cultured or extracted from acellular material collected from a subject (for example from the blood plasma of a subject). In some embodiments the plasma membrane may be harvested from a different subject from the subject to be treated. In other embodiments the plasma membrane may be harvested from the same subject from that to be treated.

It is to be understood that the anionic lipid according to all aspects of the invention may not necessarily be the only lipid present in the anionic lipid coating. Other lipids which be neutral, anionic or cationic may also be present. However, an overall negative charge must predominate on the lipids of the anionic coating. The preponderance of negatively charged lipids in plasma membranes will ensure an overall negative charge.

The cationic coating consist mainly of lipid, but may contain other material, for example material derived from the cell or exosomes wherein the lipid is extracted from a plasmalemma. Preferably, at least 70, 80 or 90% by weight of the cationic coating is lipid. Preferably, at least 2, 3 or 5% (by weight or molar ratio) or the lipid of the cationic coating is PEGylated lipid. The PEGylated lipid may be a fraction of the lipid extracted from a plasmalemma, but in most embodiments it will be pre-PEGylated lipid mixed with lipid extracted from a plasmalemma.

In some embodiments, the methods of the invention involve using lipid which has previously been extracted (i.e. the step of extracting the lipid is not claimed). In other embodiments, the methods of the invention include the additional step of extracting the lipid but do not claims the steps of obtaining the cells from the subject. In other embodiments, the methods of the invention include the steps of obtaining cells from the subject and extracting the lipid from the plasma membrane of those cells.

PEGylation

The anionic coating preferably comprises PEGylated lipids. PEGylation is the process of covalent attachment of polyethylene glycol (PEG) to a lipid. Various length PEGs can be used in accordance with all aspects of the invention. For example the invention in all aspects may use PEG 500 to PEG 5000, for example PEG 700 to PEG 4000, for example PEG 800 to PEG 3000, for example PEG 1000 to PEG 2500, for example PEG 1800 to PEG 2200 (in accordance with convention the number designates the average molecular weight of the PEG molecule). In accordance with the invention PEGylated lipids may be introduced into the anionic lipid bilayer of the particle's coating by mixing pre-PEGylated lipids for example PEG2000-DPPE, PEG2000-DOPE, PEG2000-DSPE into a lipid bilayer formed from lipids previously extracted from a plasma membrane. Alternatively or additionally, the lipids of the plasma membrane. In either case the proportion of PEGylated molecules may preferably be at least 2, 5, 10 20 or 30% of the total number of lipid molecules in accordance with certain embodiments. In other embodiments no more of 1, 2, or 3% of the total number of lipid molecules are PEGylated. In some embodiments the total number of lipid molecules which are PEGylated lies between 1 and 5%, for example between 1 and 3% or between 1 and 2% or between 1.5 and 3%. PEGylation of the coating may be carried out using any commercially available method, for example by co-formulation using a lipids in a rotary evaporating to make liposomes by thin film or by a dehydration/rehydration process PEGylation typically increases the half-life of the complex in vivo. In most embodiments, the PEGylated lipids will be added the anionic coating by mixing pre-PEGylated lipids with the rest of the components of the coating. PEGylated lipids are typically water soluble but because the lipid component of the PEGylated lipid is stabilised when it inserts itself into a lipid bilayer, it is possible to add PEGylated lipids to a liposome bilayer anionic coating in accordance with the invention simply by adding PEGylated lipid to the aqueous solution in which the nascent complexes of the invention are suspended Any available method of lipid PEGylation may be used in according with all aspects of the invention. A variety of PEGylation agents are commercially available, for example from ThermoScientific.

Nucleic Acid

According to certain embodiments the nucleic acid is an mRNA. According to other embodiments it is an interfering RNA (RNAi). RNAi may be micro interfering RNA (miRNA) or small interfering RNA (siRNA). In some embodiments, the RNAi may be antiviral or anticancer. For example, it may be an siRNA which silences a gene differentially upregulated in cancer cells.

According to certain embodiments, the nucleic acid may be between 15 and 30 base pairs, or between 50 and 500 base pairs long (for example between 18 and 28, 60 and 400, 200 and 500, 300 and 500 base pairs long). RNA may be single or double stranded.

According to other embodiments the nucleic acid is DNA. According to embodiments relating to the treatment of cystic fibrosis, the nucleic acid comprises a sequence encoding the cystic fibrosis transmembrane conductance regulator (CFTR), optionally operably linked to a promotor sequence active in human lung epithelial cells. In such embodiments, the cell surface binding component preferably binds to the cell surface of human lung epithelial cells. In such embodiments the anionic coating preferably comprises a lipid composition wherein said lipids vary from the lipid composition of the plasmalemma of human lung epithelium cells by no more than 20%. Optionally, the anionic coating may be derived, at least in part from human lung epithelial cells (for example a human lung epithelium cell line or primary culture, which may optionally be autologous with the subject to be treated).

Non-Viral Delivery Complex Particle Size

It is preferred in accordance with all aspects of the invention, that the non-viral delivery complexes have a particle size of less than 500 nm, for example less than 250 nm, for example less than 100 nm. In a population of particles there will be some variation in particle size but the above criteria will be taken as met if at least 80% of the particles are of less than 500 nm, for example less than 250 nm, for example less than 100 nm.

Pharmaceutical Carriers

Pharmaceutical compositions of the invention may comprise a non-viral delivery complexes of the invention admixed with a pharmaceutically acceptable excipient, for example an excipient suitable for a specific route of administration. The composition may also be provided in a suitable storage or delivery device. For example, the composition may be formulated with excipients (for examples powders and/or aerosol propellants) suitable for delivery by inhalation for delivery to the lungs. In such embodiments in may optionally be packaged in an inhaler canister. It may be formulated in a solution for IV injection and optional packaged in a syringe or other injection device. It may be formulated into a cream, ointment or lotion for delivery to the skin or other body surface or it may be formulated for intratumoural or intraperitoneal injection.

Diseases to be Treated

Specific diseases contemplated for treatment by the non-viral delivery complexes and/or pharmaceutical compositions of the invention include respiratory diseases including cystic fibrosis, primary ciliary dyskinesia, COPD and asthma, and also cancer both of the respiratory system and at other body sites. According to all aspects of the invention the cell surface receptor binding component may optionally be selected to bind to a cell type chosen with reference to the disease to be treated. According to some embodiments the cell type is an epithelial cell type for example a respiratory epithelial cell type such as a ciliated columnar cell, a goblet cell or a basal cell; a skin epithelial cell type, a nasal or gut epithelial cell type, or an epithelial cell type of the blood vessels, submandibular glands, gingiva, tongue, palate, oesophagus, stomach, small intestine, large intestine, rectum, anus, gallbladder, thyroid, lymph vessel, skin, mesothelium, ovaries, fallopian tubes, uterine endometrium, cervix, vagina, epididymis, vas deferens, larynx, trachea, kidney, prostate, nose or cornea.

EXAMPLES

Unless otherwise noted, solvents and reagents for synthesis were reagent grade from commercial suppliers and used without further purification. Dry $CH_2Cl_2$ was obtained using anhydrous alumina columns using the procedure described in Pangborn, A. B.; Giardello, M. A.; Grubbs, R. H.; Rosen, R. K.; Timmers, F. J. *Organometallics* 1996, 15, 1518-1520. All moisture-sensitive reactions were performed under a nitrogen or argon atmosphere using oven-dried glassware. Reactions were monitored by TLC on Kieselgel 60 $F_{254}$ plates with detection by UV, potassium permanganate, and phosphomolybdic acid stains. Flash column chromatography was carried out using silica gel (particle size 40-63 μm). $^1H$ NMR and $^{13}C$ NMR spectra were recorded on a Bruker AMX300 MHz, Avance-500 MHz and Avance-600 MHz machines. Coupling constants are measure in Hertz (Hz) and unless otherwise specified, spectra were acquired at 298 K. Mass spectra were recorded on Thermo Finnegan MAT 900XP, Micromass Quattro LC electrospray and VG70-SE mass spectrometers. Infrared spectra were recorded on a Shimadzu FTIR-8700 spectrometer.

In the following examples the liposomes are denoted using the abbreviation "Cnn DXXX nn", where Cnn is the cationic lipid, e.g. C14 (DTDTMA), C18 (DOTMA) or C16 (DHDTMA); DXXX is the phospholipid, e.g. DOPE (phosphatidyl ethanolamine or 1,2-dioleoyl-sn-glycero-3-phosphoethanolamine), DOPC (phosphatidyl choline or 1,2-dioleoyl-sn-glycero-3-phosphocholine) or DSPC (1,2-distearoyl-sn-glycero-3-phosphocholine); and nn is the peptide, e.g. ME27 (27), Peptide 35 (35), Y (Y) or Peptide 32 (32).

Lipids

DTDTMA (C14), DOTMA (C18) and DHDTMA (C16) were prepared according to the method described in Hurley C A, Wong J B, Hailes H C and Tabor A B, *Assymetric Synthesis of Dialkyloxy-3-alkylammonium Cationic Lipids*. J. Org. Chem. 2004, 69:980-983.

DOPE is available from Avanti Polar Lipids, Alabaster, Ala., USA.

DSPC is available from Avanti Polar Lipids, Alabaster, Ala., USA.

DOPC is available from Avanti Polar Lipids, Alabaster, Ala., USA.

Peptide Synthesis

The peptides described (Table IA) were synthesized using standard instruments and techniques.

TABLE 1A

Peptide sequence

| Peptide | Sequence |
| --- | --- |
| K16 | KKKKKKKKKKKKKKKK (SEQ ID NO: 3) |
| ME27 | (K)$_{16}$RVRRGACRGDCLG (SEQ ID NO: 15) |
| Peptide 32 | (K)$_{16}$RVRRGACYGLPHKFCG (SEQ ID NO: 14) |
| Y | (K)$_{16}$GACYGLPHKFCG (SEQ ID NO: 16) |
| Peptide 35* | (K)$_{16}$RVRRXSXGACYGLPHKFCG (SEQ ID NO: 13) |

*in peptide 35 X = ε - Ahx

TABLE 1B

Peptide mass

| Peptide | Mass (g · mol$^{-1}$) |
| --- | --- |
| K16 | 2068 |
| ME27 | 3467.5 |
| Peptide 35 | 4184.38 |
| Y | 3303.28 |
| Peptide 32 | 3870.98 |

Linear peptide sequences: The peptide was synthesized on a 20 µmol scale using 2 ml syringes with Teflon fits and 500 µl coupling volume. Fmoc-Gly preloaded NovaSyn TGT resin or Fmoc-Gly-2-Cl-Trt-resin were used for these sequences. Fmoc-Peg4-COOH was synthesized following a procedure reported previously (see synthesis of Fmoc-Haa4-COOH at page 82 of WO 2005/117985—Fmoc-Haa4-COOH was the name given to Fmoc-Peg4-COOH in that specification). The TGT resin was initially swelled for 10 min, however the 2-Cl-Trt resin needed a prolonged initial swelling time (some hours) in DMF. Routine coupling was performed with HBTU (in DMF) and DIPEA (in NMP) using a fourfold excess of reagents. Fmoc was cleaved with a 40% solution of piperidine in DMF for 3 min and a 20% solution for 10 min Synthesis cycles consisted of 40 min coupling time, 3 min for Fmoc deprotection with 40% piperidine, another 10 min for Fmoc deprotection with 20% piperidine and washing steps. After synthesis and the last wash cycle with DMF, peptides were washed with DCM, methanol and diethyl ether (3 times each) using the "manual"/"empty" function of the Syro. Suction was applied for some more time to help evaporate the ether.

On-resin disulfide bond formation: To form disulphide bridges on resin, the resin was placed in a syringe with PE frit and swelled in DMF. After removal of excess DMF a freshly prepared solution of iodine in a minimum amount of DMF (e.g. 500 µl for a 2 ml syringe, 10 eq iodine to resin loading) was added and the syringe was vortexed during 4 h for 20 s every 4 min. The reagent solution was removed and the resin was washed 10 to 20 times with DMF, and 3 times each with DCM, methanol and ether.

Cleavage and deprotection: The syringes were transferred to the fume hood for cleavage. Cleavage was performed with a cocktail of 95% TFA, 2.5% TIS and 2.5% H$_2$O. A minimum amount of freshly prepared cocktail was added to cover the resin (e.g. <500 µl in the 2 ml syringes). After 4 h the cleavage solutions were passed into polypropylene (PP) tubes using a plunger and the resins were washed with another small amount of cleavage cocktail (e.g. 200 µl in the 2 ml syringes). Then the peptides were precipitated with ether (e.g. to the combined fractions of the 2 ml syringes some 4 ml of diethyl ether were added). The PP tubes were kept in the freezer for at least 15 min, then centrifuged at 3000 rpm for 3 min and solution was decanted from the peptide pellet. Centrifugation and decantation were repeated twice with about 2 ml of ether.

Finally the peptides were dissolved in water or tBuOH/water (4:1) and freeze-dried. Some peptide sequences showed very poor solubility and sometimes several lyophilisation/dissolution processes with different solvent mixtures (water, tBuOH or acetonitrile) were necessary to obtain a fluffy peptide.

The peptide was analyzed by reverse phase HPLC and purified by reverse phase HPLC to >90% pure. Mass spectra were recorded using the Micromass Quattro ES-MS (Software: Masslynx) and the masses are recorded in the table 1B.

Peptide 35, K16Y and Peptide 32 were purchased from AMS Bio Ltd., Birmingham, UK, and synthesised using semi-automated peptide synthesis chemistry. The peptide was analysed by reverse phase HPLC and purified where necessary by reverse phase HPLC to 85% pure. Relative molecular masses are given in the table 1B.

K16 was purchased as described previously (Hart et al., Lipid-mediated enhancement of transfection by a nonviral integrin-targeting vector. *Hum Gene Ther.*, 1998, 9, 575-585). Relative molecular masses are given in the table 1B.

All these freeze-dried peptides were diluted at 10 mg/ml in water and stored at −20° C. during several months. Once thawing, aliquots of peptides are kept at 4° C. during several weeks.

mRNA mRNA coding for firefly luciferase (CleanCap FLuc mRNA) was purchased from TriLink Biotech, San Diego, Calif. Both mRNA with no modifications and with psuedouridine modifications were used.

Particle Imaging

The size of RLP nanoparticles containing peptides with lipids were determined at different weight ratios of liposome to mRNA (w/w) by dynamic light scattering using a NanoZS Zetasizer (Malvern). Complexes were prepared as described above except that they were formulated in nuclease-free water rather than Opti-MEM. Samples of 1 mL (containing 1.5 µg of mRNA) were analysed to determine their size and zeta potential. The size was recorded as the average of the intensity-based distribution of particles.

Preparation of Various Non-Viral Nanocomplexes of the Invention

Weight Ratio for the Preparation of LPRL-RTN (Lipid/Peptide/mRNA/Lipid-Receptor Targeted Nanoparticles, DD=DOTMA-DOPE Mixture)

| RTNs (RTN = receptor targeted nanocomplexes) | Inner Cationic Core LPR-RTN | Weight Ratio of Inner Cationic Core LPR-RTN, Lipid mixture:peptide:nucleic acid ratio | Outer Anionic Liposome (see table below) | Weight Ratio of Anionic Liposome |
|---|---|---|---|---|
| LPRL1-RTN | DD/ME27/siRNA | 0.75/3/1 | GK24 | 20 |
| LPRL2-RTN | DD/ME27/siRNA | 1/3/1 | GK24 | 20 |
| LPRL3-RTN | DD/ME27/siRNA | 0.75/3/1 | AT3 | 19 |
| LPRL4-RTN | DD/ME27/siRNA | 0.75/3/1 | AT4 | 10.84 |
| LPRL5-RTN | DD/ME27/siRNA | 0.75/3/1 | AT5 | 9.9 |
| LPRL6-RTN | DD/ME27/siRNA | 0.75/3/1 | AT6 | 14 |
| LPRL7-RTN | DD/ME27/siRNA | 0.75/3/1 | AT7 | 13.5 |

Note:
The weight ratios were optimized in order to obtain anionic LPRL-RTNs with minimal liposome and peptide usage.

Composition of Out Liposome Coating

| Liposome | Lipid 1 (molar %) | Lipid 2 (molar %) | Lipid 3 (molar %) |
|---|---|---|---|
| GK24 | DOPG (47.5%) | DOPE (47.5%) | mDPPE-PEG2000 (5%) |
| GK25 | DOPG (47.5%) | DOPE (47.5%) | DOPE-PEG2000 (5%) |
| GK27 | DOTMA (47.5%) | DOPE (47.5%) | mDPPE-PEG2000 (5%) |
| GK28 | DOTMA (47.5%) | DOPE (47.5%) | DOPE-PEG2000 (5%) |
| AT1 | DOTMA (49.5%) | DOPE (49.5%) | mDPPE-PEG2000 (1%) |
| AT2 | DOTMA (49.5%) | DOPE (49.5%) | DOPE-PEG2000 (1%) |
| AT3 | DOPG (49.5%) | DOPE (49.5%) | mDPPE-PEG2000 (1%) |
| AT4 | DOPG (95%) | — | mDPPE-PEG2000 (5%) |
| AT5 | DOPG (99%) | — | mDPPE-PEG2000 (1%) |
| AT6 | DOPG (71.25%) | DOPE (23.75%) | mDPPE-PEG2000 (5%) |
| AT7 | DOPG (74.25%) | DOPE (24.75%) | mDPPE-PEG2000 (1%) |

LPRL1-RTN to LPRL7-RTN were prepared using components as indicated in the table above using the methods described herein and placed in normal phosphate buffered saline (Thermofisher (formerly Life Technologies), cat no. 14190-094). PBS buffer for up to 4 hours. The size of the particles were then analyzed as described above.

Exosome Production

Exosomes may be harvested from any suitable body fluid or a cell culture medium. As an example to illustrate how exosomes can be harvested from a cell culture, the U937 cell line was grown in 1640 RPMI medium supplemented with 10% fetal bovine serum (FBS). U937 cells were grown in suspension and were expanded in upright T75 flasks in approximately 30 ml of media. Cultures were passaged every 3-4 days and new media added every second day if required. The cell line was expanded until there were at least eight T75 flasks to have sufficient number of cells ($1.5 \times 10^6$ to $2.0 \times 10^6$ cells per flask).

For exosome extraction, U937 must be grown in conditioned media to prevent contamination from FBS serum which is rich in fetal bovine exosomes. U937 cell lines were cultured in media as described above. At least 2 days before harvesting of exosomes, they were switched to conditioned media. Extraction and purification protocols were taken from Thery et al., 2006—isolating and characterization of exosomes from cell culture supernatants and biological fluids, *Current Protocols in Cell Biology*.

The conditioned media (exosome-free media) was prepared as follows:

1. To 1640 RPMI media was added 20% FBS.
2. This complete media was centrifuged in 38 ml polycarbonate tubes at 100,000 g at 4° C. overnight in an ultracentrifuge (Beckman Coulter Optima XPN-100 Ultracentrifuge).
3. The supernatant was removed making sure that the pellet (not always present) was not disturbed, and filter sterilized with 0.22 μm filters.
4. This conditioned media was diluted with equal volumes of 1640 RPMI media which is free of FBS.
5. Conditioned media can be stored at 4° C. for up to 4 weeks.

Extraction of Cell Lipids

This protocol for harvesting of phospholipids from cell culture was adapted from the Bligh and Dyer method (1959) J. Biochem, Physiol. 37(8):911-7. Essentially, specific ratios of chloroform, methanol and water were mixed to ensure liquid phase separation based on hydrophobic/hydrophilic interactions of the proteins, carbohydrates and lipids present in cell membranes.

1. U937 cells at a density of $3 \times 10^6$ were centrifuged for 5 minutes at 1200 g in a 15 ml Falcon tube. The supernatant was discarded and the cell pellet washed three times in Phosphate buffered saline solution (PBS).
2. 1 ml of PBS was added to pellet and resuspended.
3. Adapted from the Bligh and Dyer method, this procedure should was performed in a vacuum hood:
   1.25 ml of chloroform was added using a Hamilton syringe to the cell pellet and vortexed.
   Then 2.5 ml of methanol was added and sample vortexed.
   1.25 ml of chloroform was added and sample vortexed.
   Finally 1.25 ml of dH$_2$O was added and sample vortexed.

4. The mixture was centrifuged for 10 minutes at 1200 g at 4° C. Three distinct phases were seen: the top layer containing the methanol/water region—all polar molecules will be in this region, a small band—this is known as the protein disc and contains the various proteins found in cells, the bottom phase contains the chloroform with non-polar molecules such as lipids.
5. The methanol phase was removed using a syringe and then using a Hamilton syringe the chloroform was carefully removed by applying positive pressure as the protein ring was pierced. Prior to adding the chloroform the test tube it was thoroughly cleaned, allowed to dry and then weighed with an accurate scientific weighing scale (MC1 Analytic AC 120S). The chloroform-lipid solution was stored in a round-bottomed flask and covered with a glass stopper at 4° C.
6. The chloroform-lipid mixture was subjected to a rotary evaporation under vacuum until a thin lipid film was seen. The test tube was then weighed and the difference between the empty test tube and the test tube containing the lipid film was calculated. This gave an approximate value for the mass of the lipids extracted.
7. DOPE was prepared to the same mass as the cell derived lipids and the two were mixed in chloroform in a 1:1 ratio and then subjected to the same evaporation, hydration and sonication protocol as described in Bligh and Dwyer.

Exosome Extraction

Exosome extraction was performed by following the Thery et al., 2006 protocol with an additional purification procedure. It was important to use as many cells as possible to ensure high yield of exosome extraction. Usually 150 ml of cell culture supernatant was sufficient.
1. U937 cell lines cultured in conditioned media as described above for 2 days were spun down at 1500 g in Falcon tubes for 10 minutes; the supernatant was collected and the pellet was discarded.
2. The supernatant was transferred to 38 ml polycarbonate tubes and centrifuged in an Ultracentrifuge at 10,000 g for 30 minutes at 4° C., collecting the supernatant and discarding the cellular debris pellet.
3. The supernatant was centrifuged at 110,000 g for 70 minutes at 4° C. The supernatant was then discarded very carefully; a small faint white pellet should be seen at the bottom of the tube. The pellet was then mixed with 300 µl of PBS and then transferred to an Eppendorf tube.
4. The exosomes were further purified using the Total Exosome Isolation Reagent (ThermoFisher, catalog number 4478359). Briefly the exosome/PBS solution was mixed thoroughly with half the volume of the kit reagent and stored in an upright position overnight at 4° C.
5. The solution was then centrifuged for 1 hour at 10,000 g at 4° C. The supernatant was discarded and the pellet of exosomes was then resuspended in 100 ul of PBS and sonicated to form liposomes.

Cationic Core Production.

Formation of the lipid/peptide/nucleic acid complexes requires the addition of the nucleic acid and peptide to the cationic lipid in aqueous solution. For cationic liposomes such as DOTMA:DOPE the core lipid was thoroughly mixed first with peptide in aqueous solution and then nucleic acid was added. The components were then incubated for 30 minutes at room temperature to form the core complexes. The mass ratios of the components is given in the table above.

Application of Coating Liposome.

According to the invention the outer coating of the delivery complex is anionic (in its net charge—it may contain individual lipid compounds having various charges). For the examples outer coatings which were anionic were prepared and so were those which were cationic for the purposes of comparison. The coating liposome was first prepared using standard liposome preparation techniques (dehydration, rehydration and sonication) and was then was applied to the core by thoroughly mixing an aqueous solution of the core complexes with the liposomes.

Example 1—Stability Comparison—Turbidity

The absorbance of complexes in triplicates in the absence and presence of different serum concentrations (0-50% v/v) was measured at 500 nm on a FLUOstar Optima spectrophotometer with a corresponding amount of serum alone as a reference. Nanocomplexes were formed as with 1 µg DNA or siRNA, incubated at 37° C. and analyzed at regular timepoints over a 30 min period. Relative turbidity was determined by dividing the sample absorbance by the time zero value in water.

Results

FIG. 1 shows the results and demonstrate that whilst simple DOTMA/DOPE liposomes and cationic liposome particles (LPRs) of the prior art are unstable over 30 minutes, the anionic PRL particles according to the invention retain stability over the course of the 30 minute experiment.

Example 2—Stability Comparison—Particle Size

Figure 2:
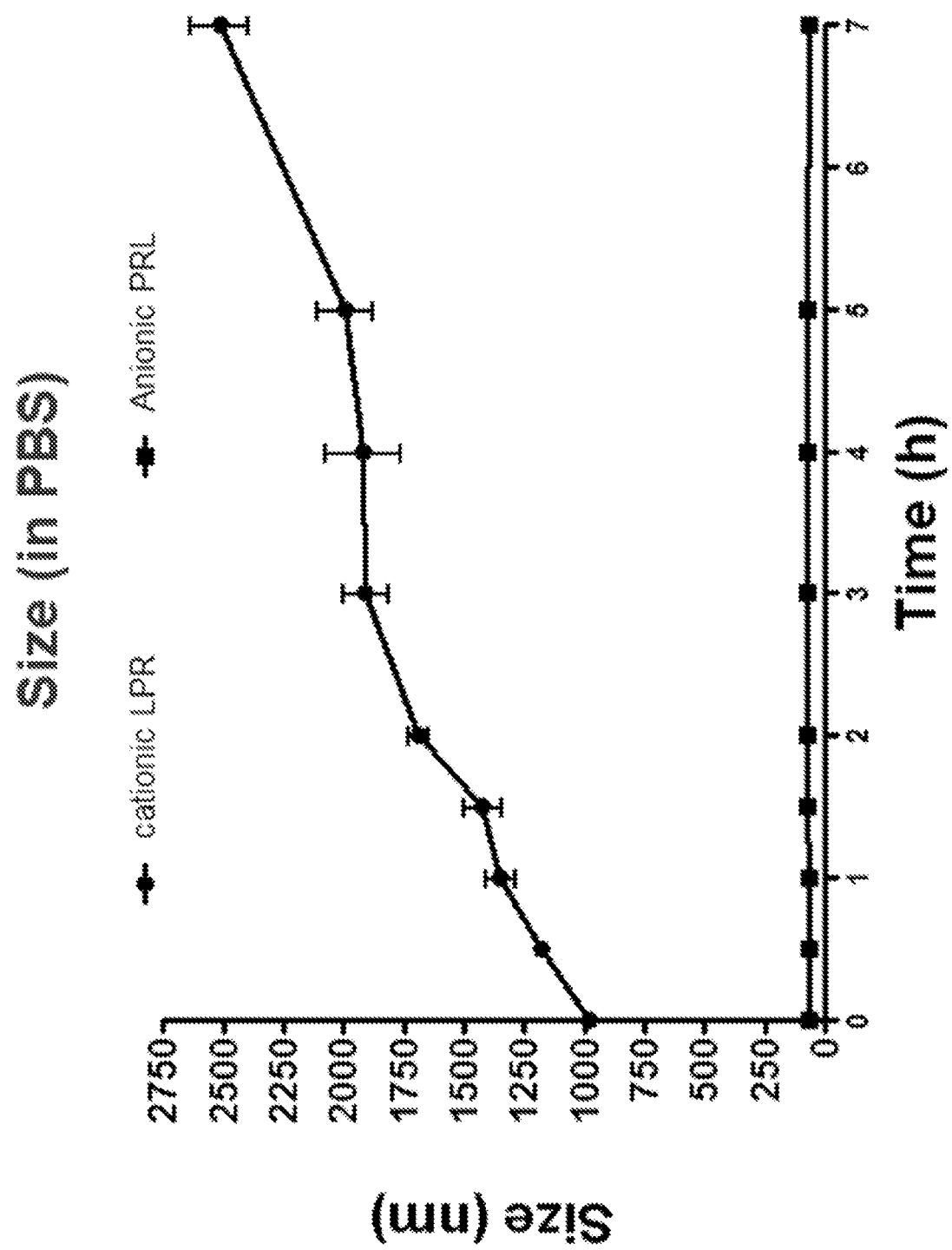
FIG. 2 shows the results of a stability comparison between non-viral delivery complexes of the invention and prior art complexes in PBS buffer.

A stability comparison experiment was carried out over 7 hours using LPR particles of the prior art and PRL complexes of the invention Results As can be seen in FIG. 2, the anionic PRL particles of the invention show stability over 7 hours which is absent in the prior art particles.

Example 3—Stability Comparison—Particle Size

A stability comparison experiment was carried out over 4 hours using various LPR particles of the invention having compositions as described above.

Results

Figure 3A:
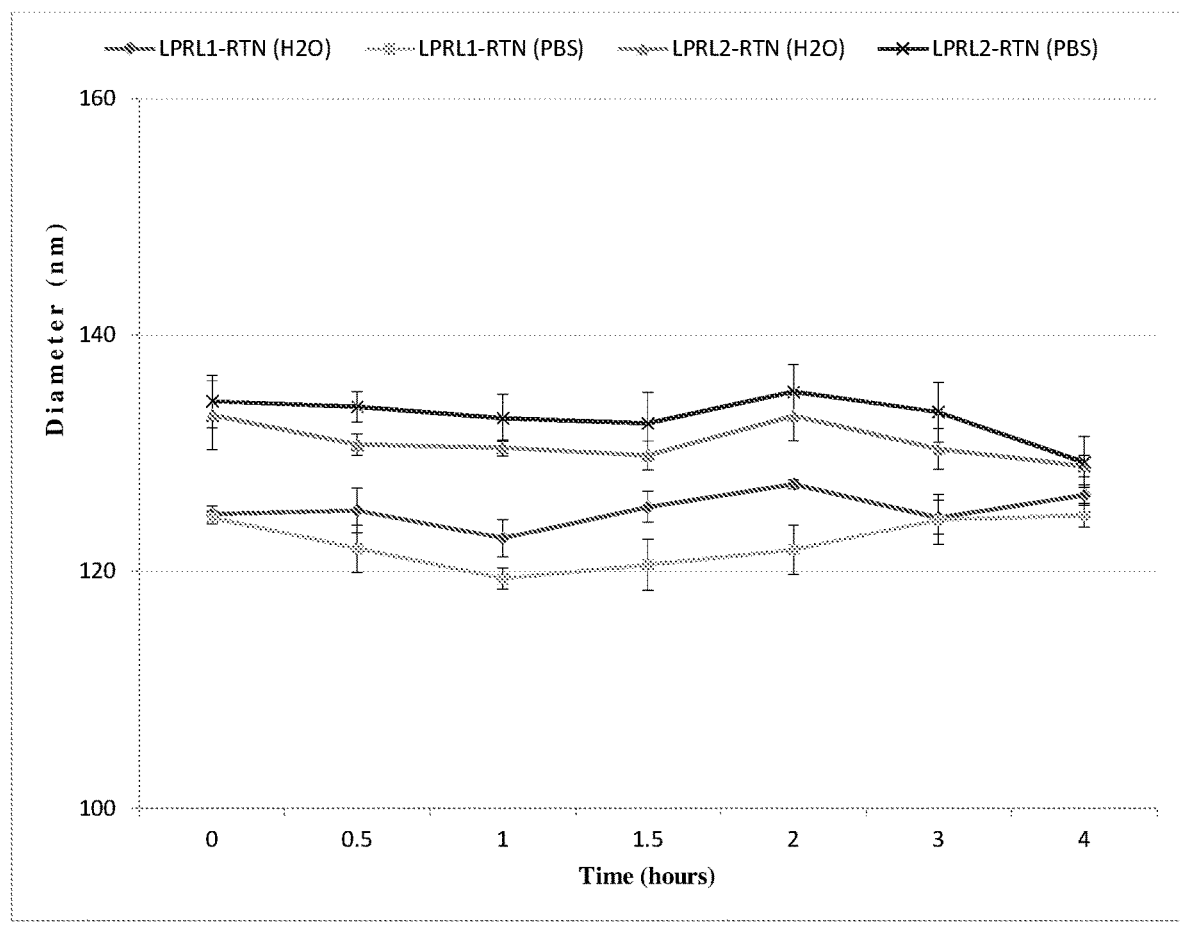
FIG. 3 shows the results of a particle size stability experiment up to 4 hours for various complexes.
Figure 3B:
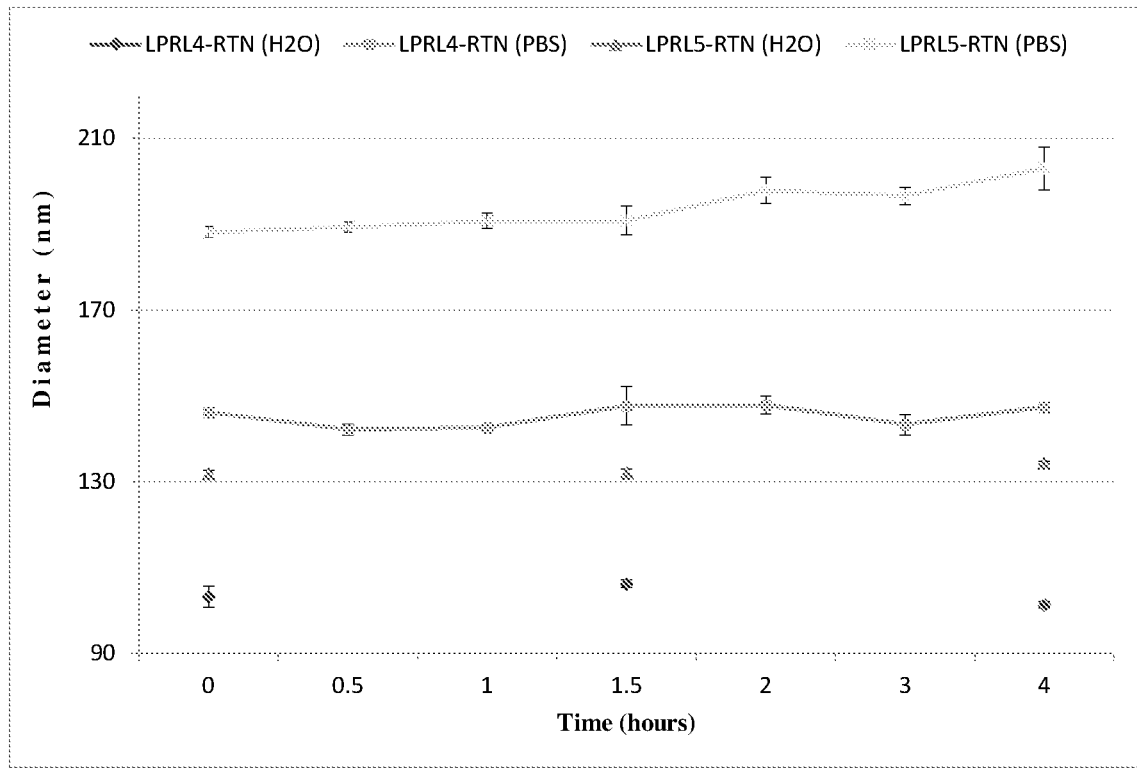
Figure 3C:
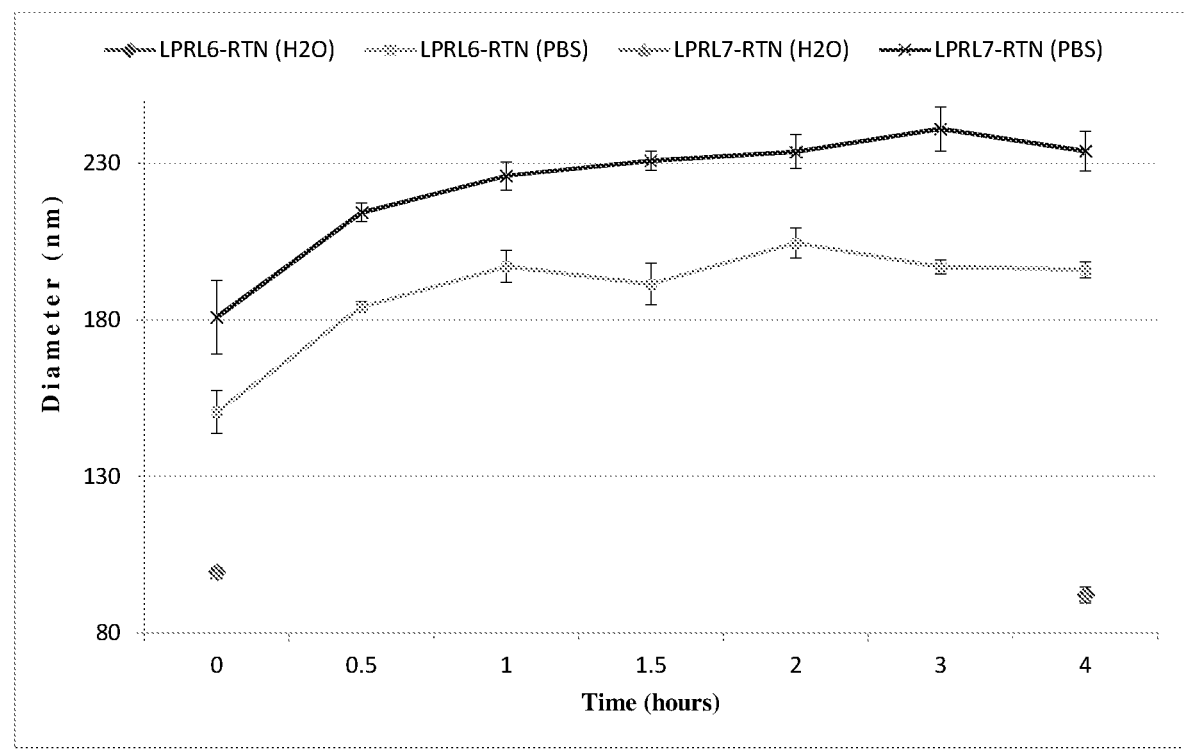
Figure 4:
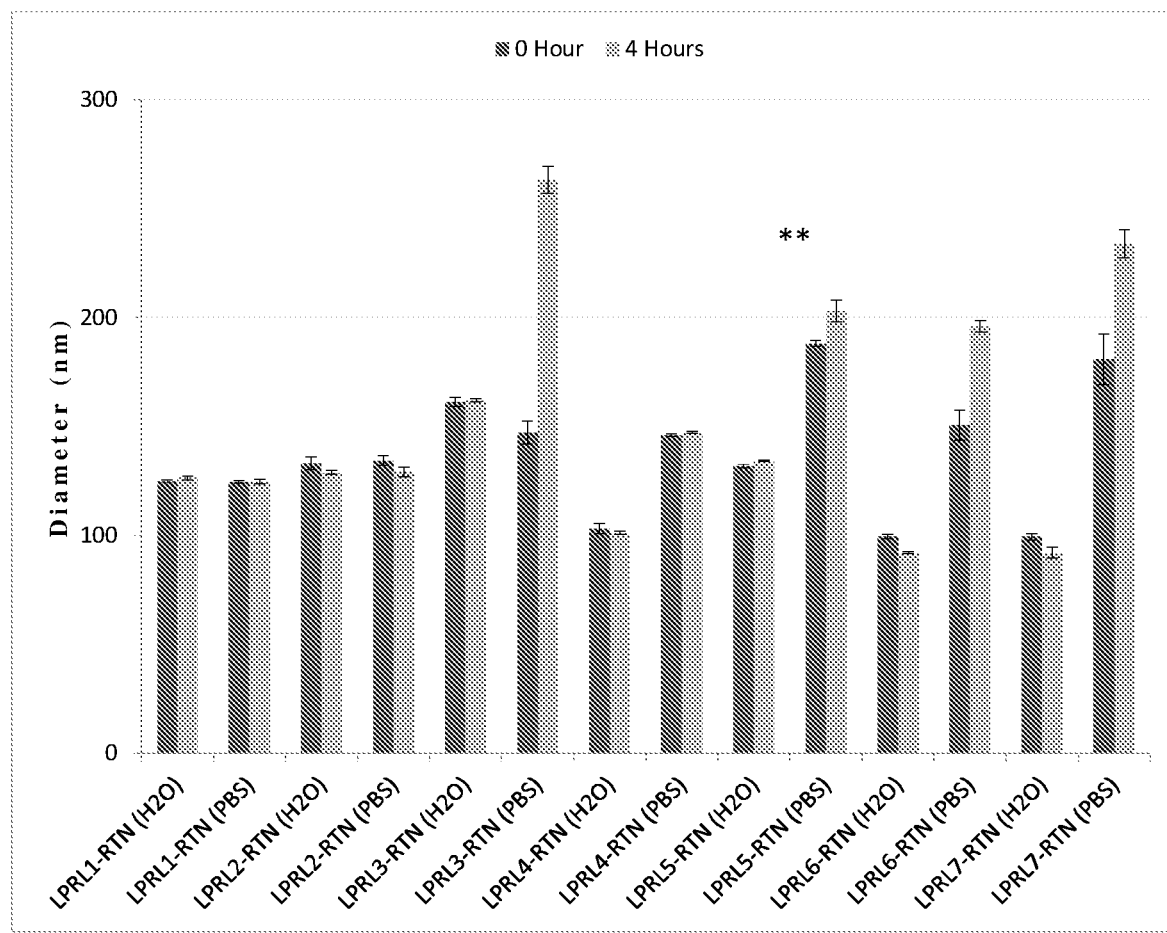
FIG. 4 shows the result of an experiment to measure particle size changes (as a surrogate for stability) of various particles of the invention as described in the examples.

FIG. 3 shows the results and FIG. 4 presents a summary of them. It can be seen that any increase in size is very small suggesting good stability. It is noted that the complexes which appear to be least stable (but still having good stability relative to prior art LPR particles) are those which have a low (1%) level of PEGylated lipid.

Example 4—Stability Comparison—Zeta Potential

Zeta potential (electrokinetic potential) is a measure of the stability of colloidal dispersions. A higher value indicates a higher degree of electrostatic repulsion between the adjacent particles. Values having a magnitude of less than 5 (i.e. from 0 to ±5) are regarded as unstable and liable to coagulation and/or flocculation. Values with a magnitude of more than 10 are regarded as having a reasonable level of stability.

Method

Zeta potential was measured as described above.

Results

Figure 5:
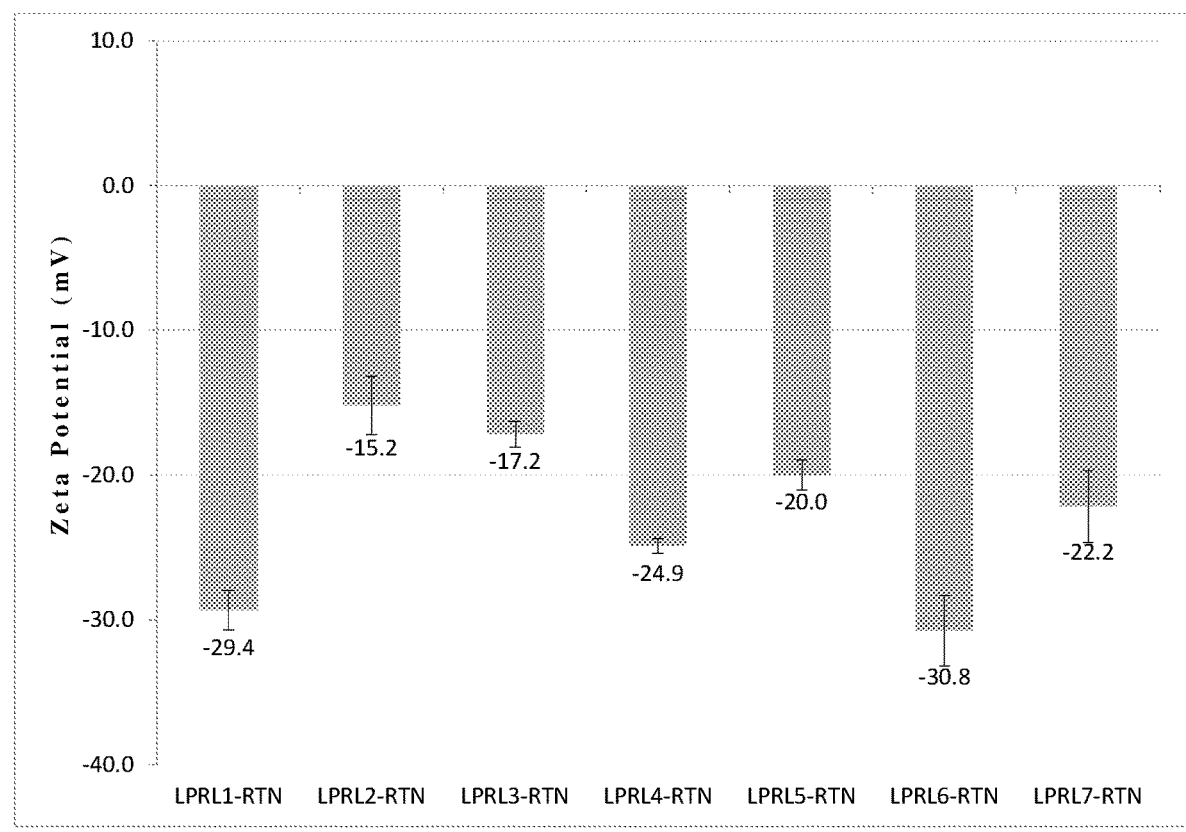
FIG. 5 shows the zeta potential of delivery complexes of the invention.

Results are shown in FIG. 5. It can be seen that for all samples of particles of the invention, the particles have a zeta potential suggestive of stability rather than coagulation/flocculation.

Example 5—Transfection Efficiency

Figure 6:
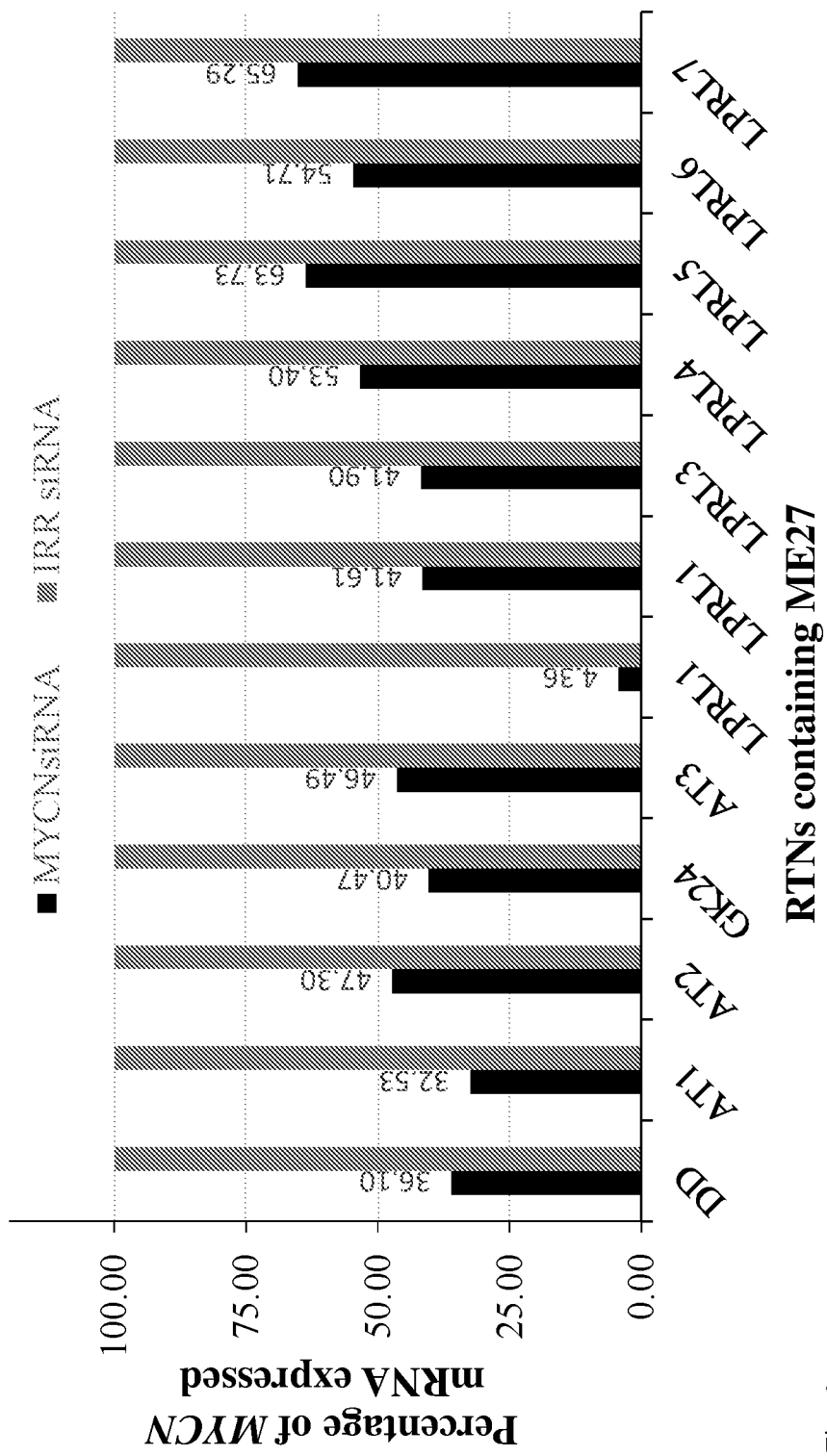
FIG. 6 shows the extent of gene expression following transfection of the gene with various vectors.
Figure 7:
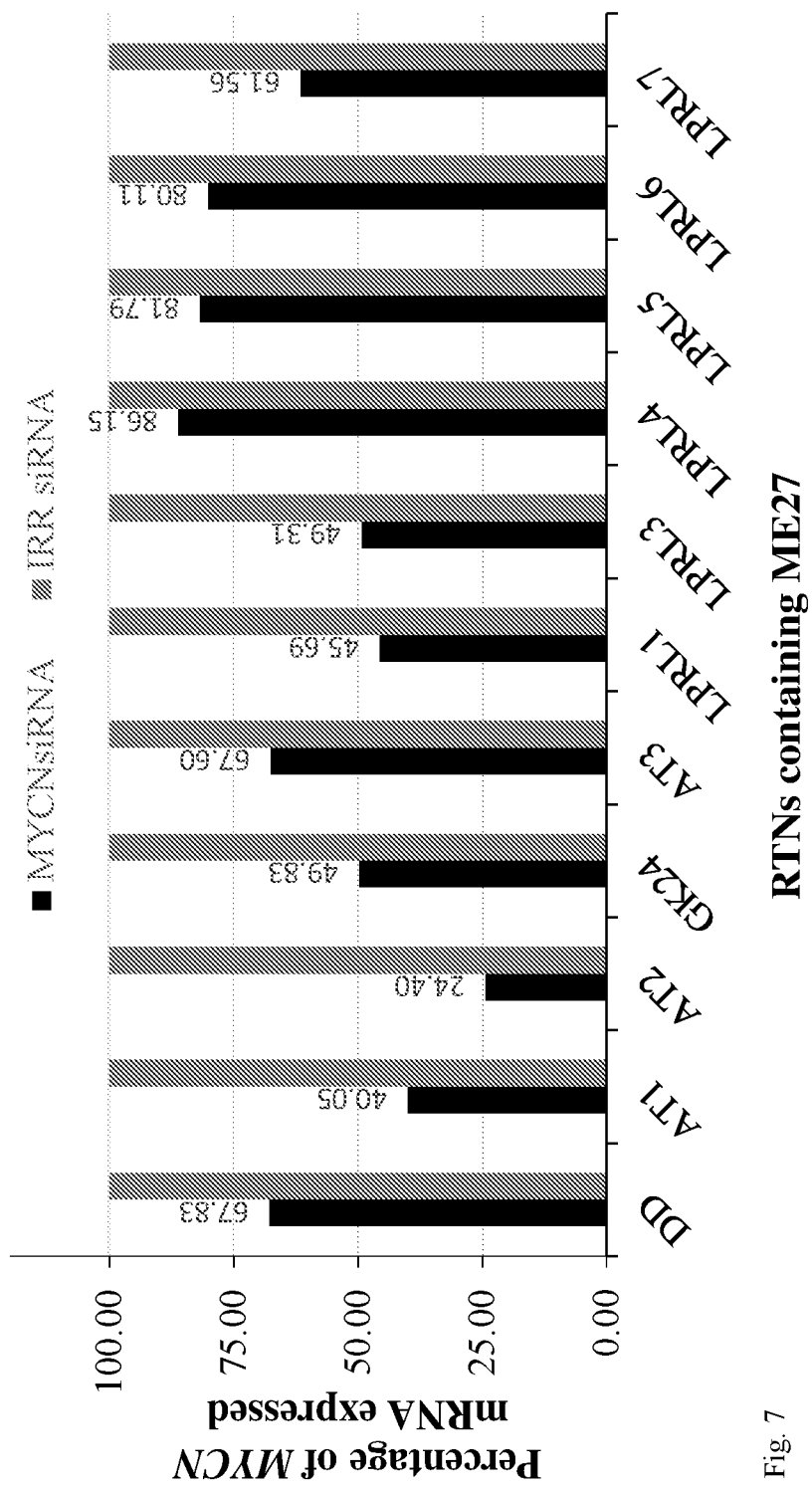
FIG. 7 shows the extent of gene expression following transfection of cells with various vectors. It shows the results of an experiment replicating that which produced the results shown in FIG. 6.

Cultured neuroblastoma cells were transfected with MYCN siRNA, using particles of the prior art (DD, AT1, AT2, GK24, AT3) or the invention (LPRL1 to LPRL7). The percentage of cells expressing MYCN mRNA has the measured and the results are shown in FIG. 6 and (in duplicate) FIG. 7. It can been seen that the non-viral complexes of the invention are successful in effecting transfection.

Example 6—Apoptosis Assay

Figure 8A:
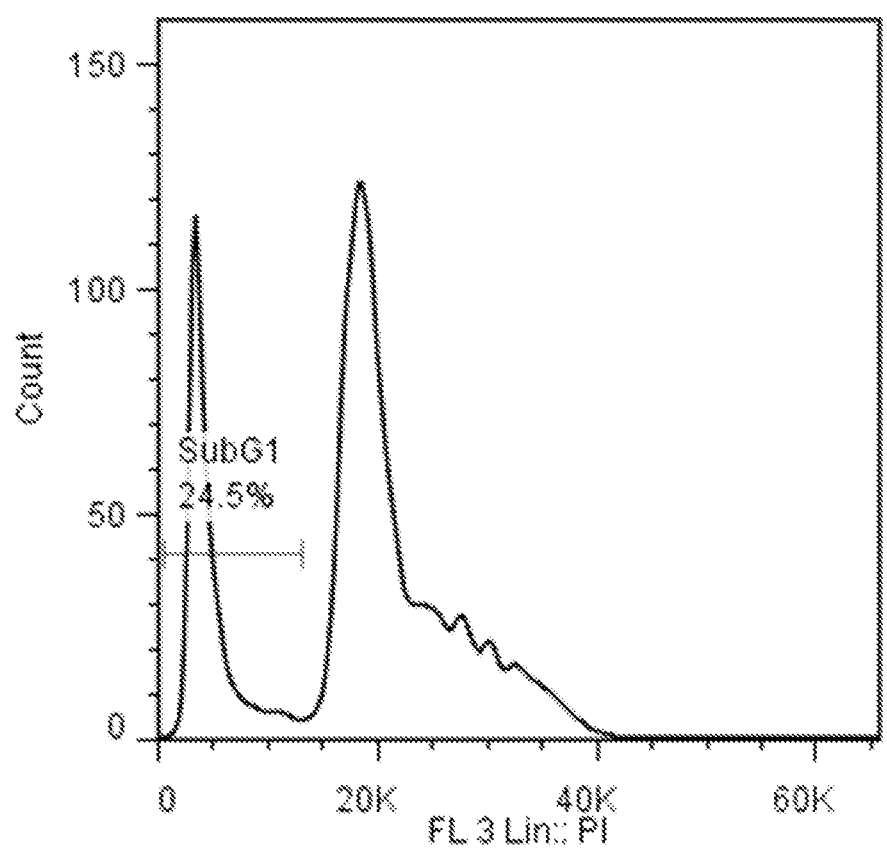
FIG. 8 shows flow cytometry data measuring apoptosis.
Figure 8B:
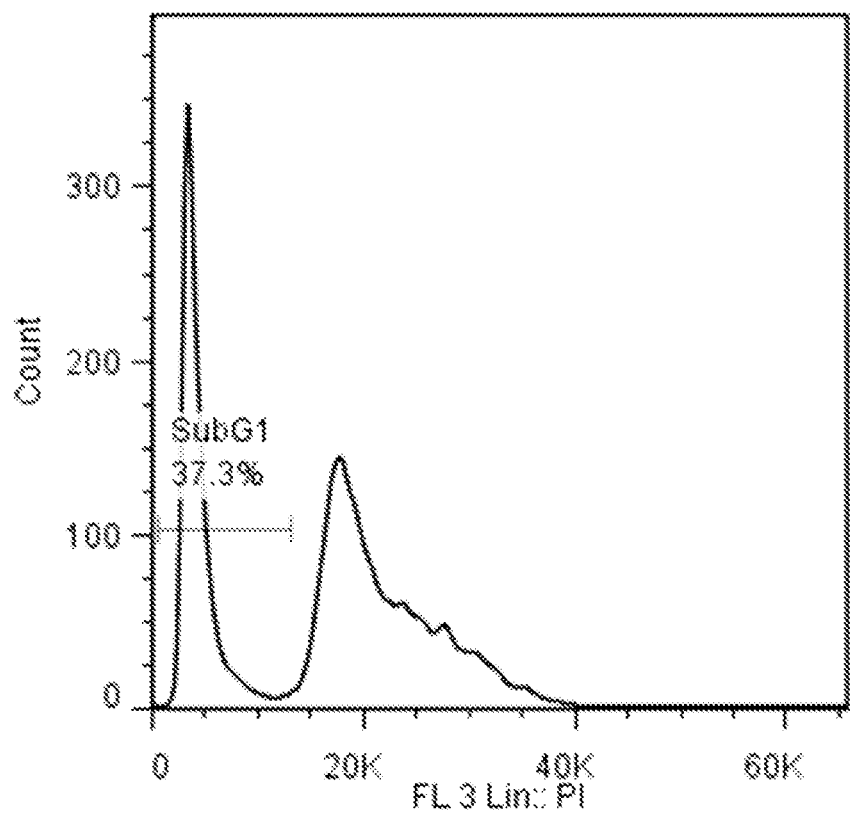
Figure 8C:
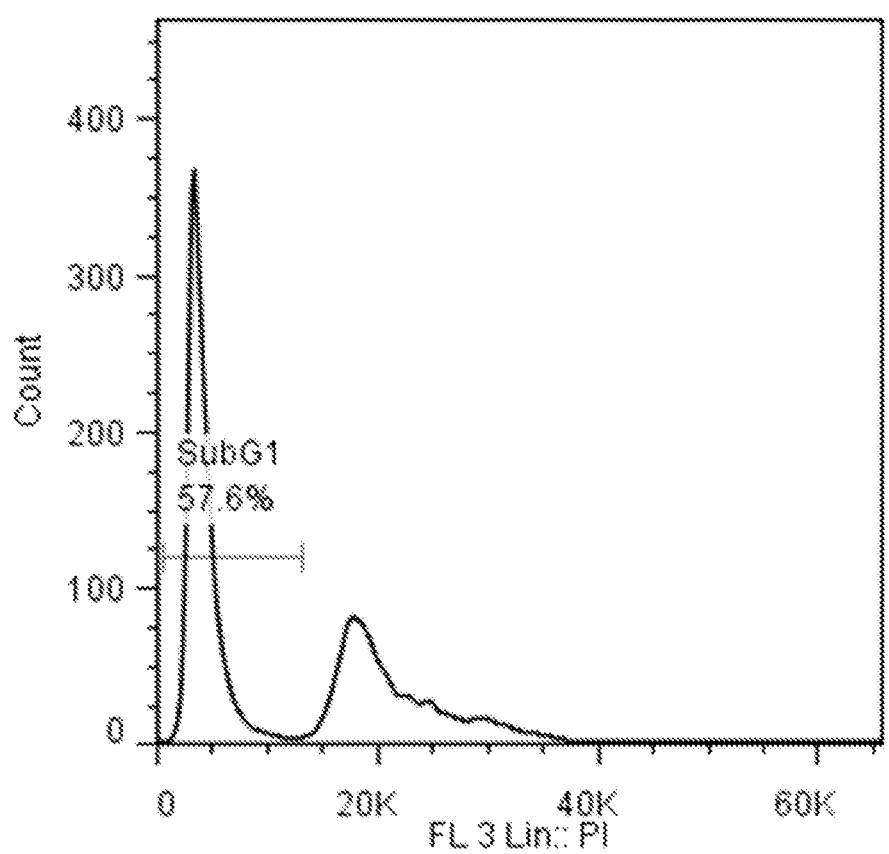

This experiment illustrates how the rapid expansion of neuroblastoma cells which are driven to rapidly expand by the oncogene MYCN can be driven to apoptose by gene silencing of MYCN by use of the MYCN siRNA of Example 5. Following transfection with the MYCN siRNA construct in various transfection complexes, cells were suspended in propidium iodide solution and analysed by flow cytometry. FIG. 8 shows the flow cytometer histograms contained. The proportion of cells showing sub-G1 levels of DNA was measured by applying the indicated gate to the histograms. FIG. 8a shows the results for prior art single layer cationic non-viral complexes ("LPR" complexes). It can be seen that 24.5% of cells have sub-G1 DNA indicative of apoptosis. FIG. 8b shows the results for prior art single layer anionic complexes ("PRL" complex). It can be seen that 37.3% of cells have sub-G1 DNA indicative of apoptosis. FIG. 8c shows the results for double layer anionic complexes of the invention ("LPRL" complexes). It can be seen that 57.6% of cells have sub-G1 DNA indicative of apoptosis. This is evidence of superior transfection efficiency of complexes of the invention compared to the prior art.

Example 7—Complexes in Cystic Fibrosis Mucus

Figure 9:
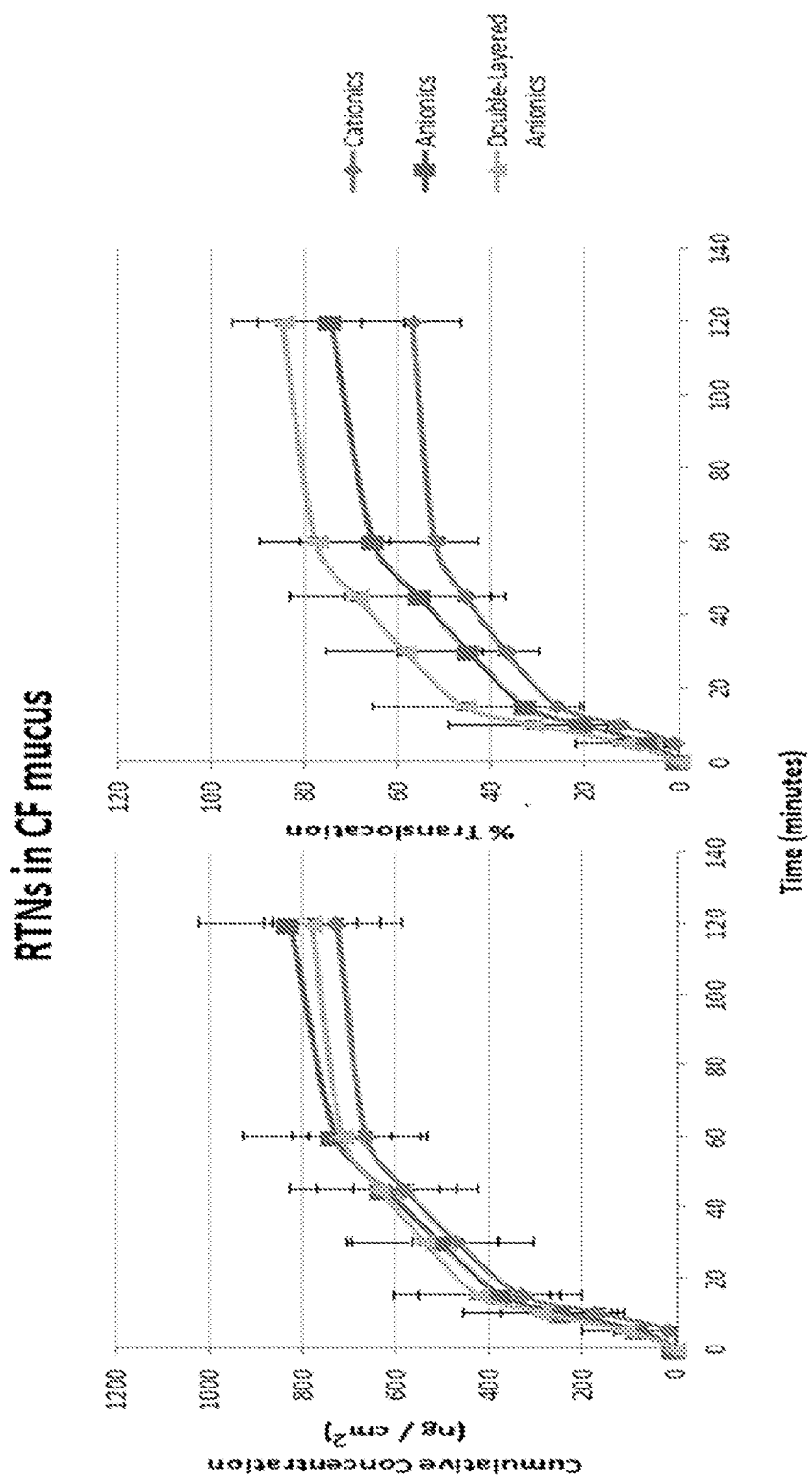
FIG. 9 shows the result of an experiment to compare the efficacy of translocation of a GFP marker genetic construct

In cystic fibrosis patients, there is a challenge in getting any gene therapy vector intact to the target cells because of the accumulation of extracellular mucus. This experiment demonstrates that the complexes of the invention can meet that challenge. A transwell mucus RTN penetration assay was carried out in 24-well plates with transwells (6.5 mm, 3.0 um pore polyester membrane inserts, Corning, UK) and kept in a 37° C. incubator. Tris-buffer was added to each well (receiver solution) and the transwell was placed on top of the buffer. 1 µl of CF or non-CF (normal) mucus (Epithelix Sarl, Geneva, Switzerland) was added on top and spread across each transwell. The plate was incubated for 30 minutes to equilibrate the mucus. 140 ng/µl siRNA RTNs were prepared and 3 ul were added to each transwell. After 5, 10, 15, 30, 45, 60 and 120 minutes, 100 µl of the tris buffer was collected and pipetted into a 96-well plate. siRNA was measured in a FLUOstar OPTIMA Microplate reader. Cumulative RTN penetration through the mucus was calculated and plotted in FIG. 9. It can be seen that complexes of the invention show good CF-mucus penetration.

Example 8—Stability Data

Figure 10:
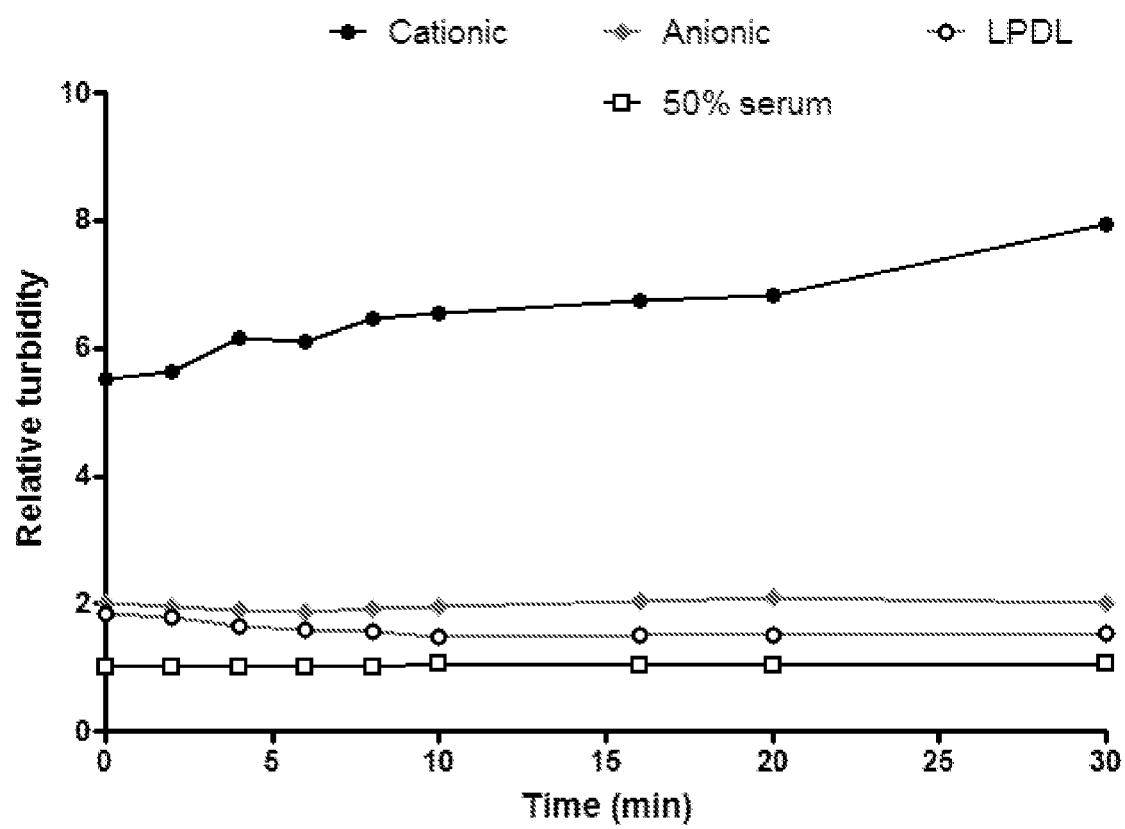
FIG. 10 shows the results of comparative stability experiments for various complexes.
Figure 11:
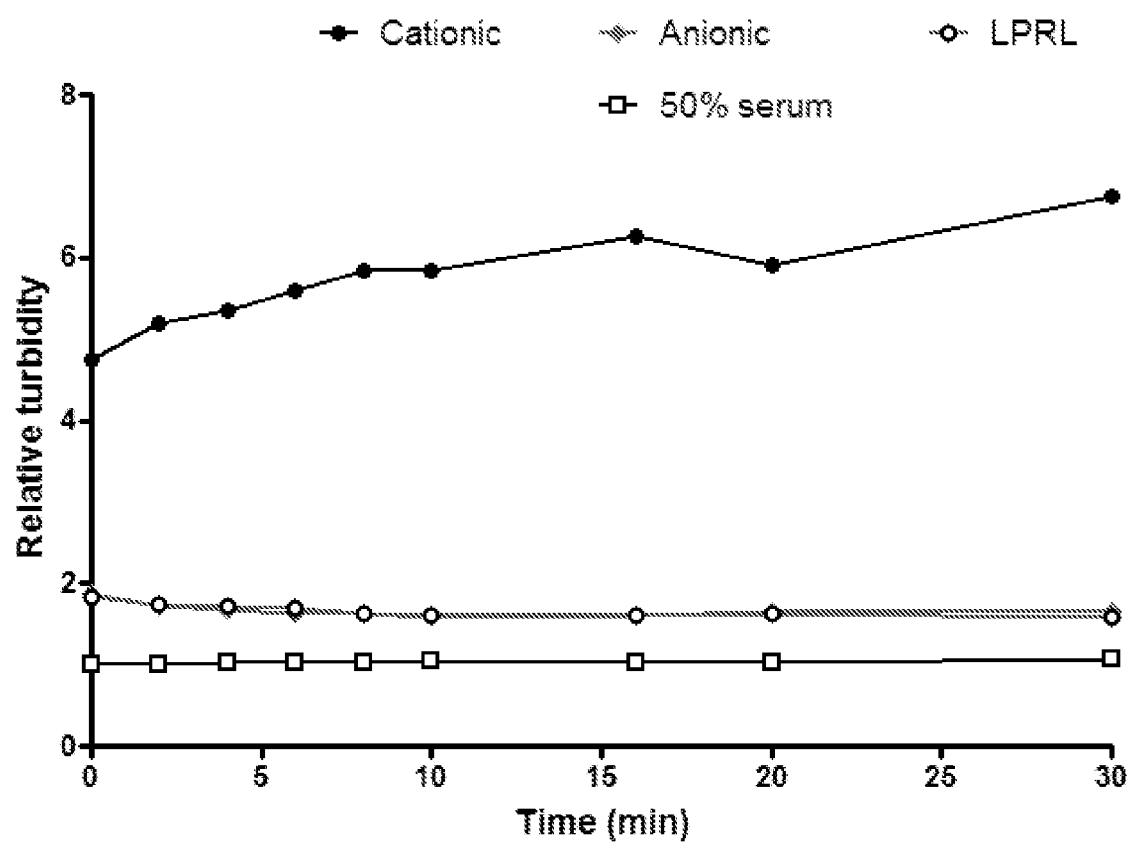
FIG. 11 shows the results of comparative stability experiments for various complexes.

FIGS. 10 and 11 show stability data as measured by changes in turbidity, measured as described in Example 1 and carried out in 50% serum. Anionic complexes and LPRL anionic complexes of the invention show reduced turbidity associated aggregation than prior art cationic complexes in 50% serum. FIG. 10 shows data from DNA-containing double layered complexes of the invention, whereas FIG. 11 shows data from siRNA-containing double layered complexes of the invention. It can be seen that both classes of complexes are stable.

Example 9—Transfection with GFP Reporter

Figure 12:
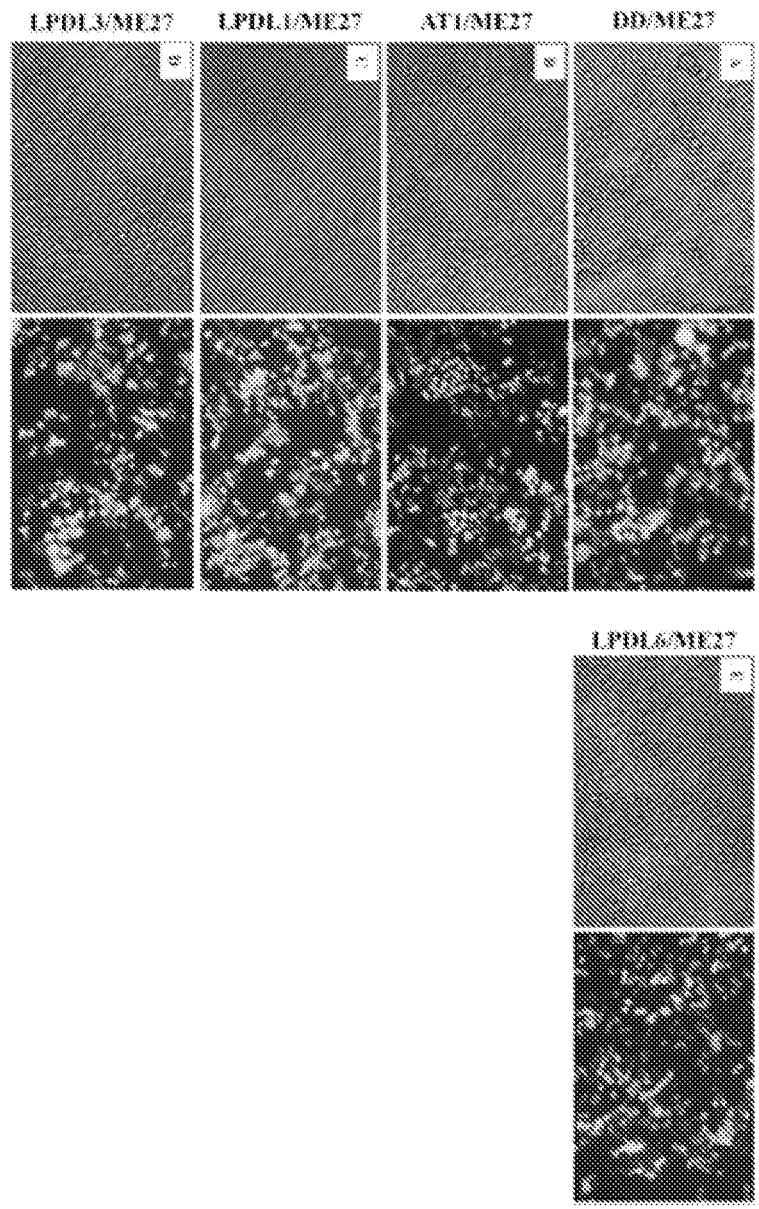
FIG. 12 shows the results of a comparison of transfection efficiencies as assessed using a GFP reporter construct. The photographs show images of N2A cells after transfection with a complex of the invention containing the reporter construct. The first photograph of each pair shows phase contrast fields of the cells and the second photograph of each pair is a fluorescence photograph showing (in green in the original) transfected cells emitting green light.
Figure 13:
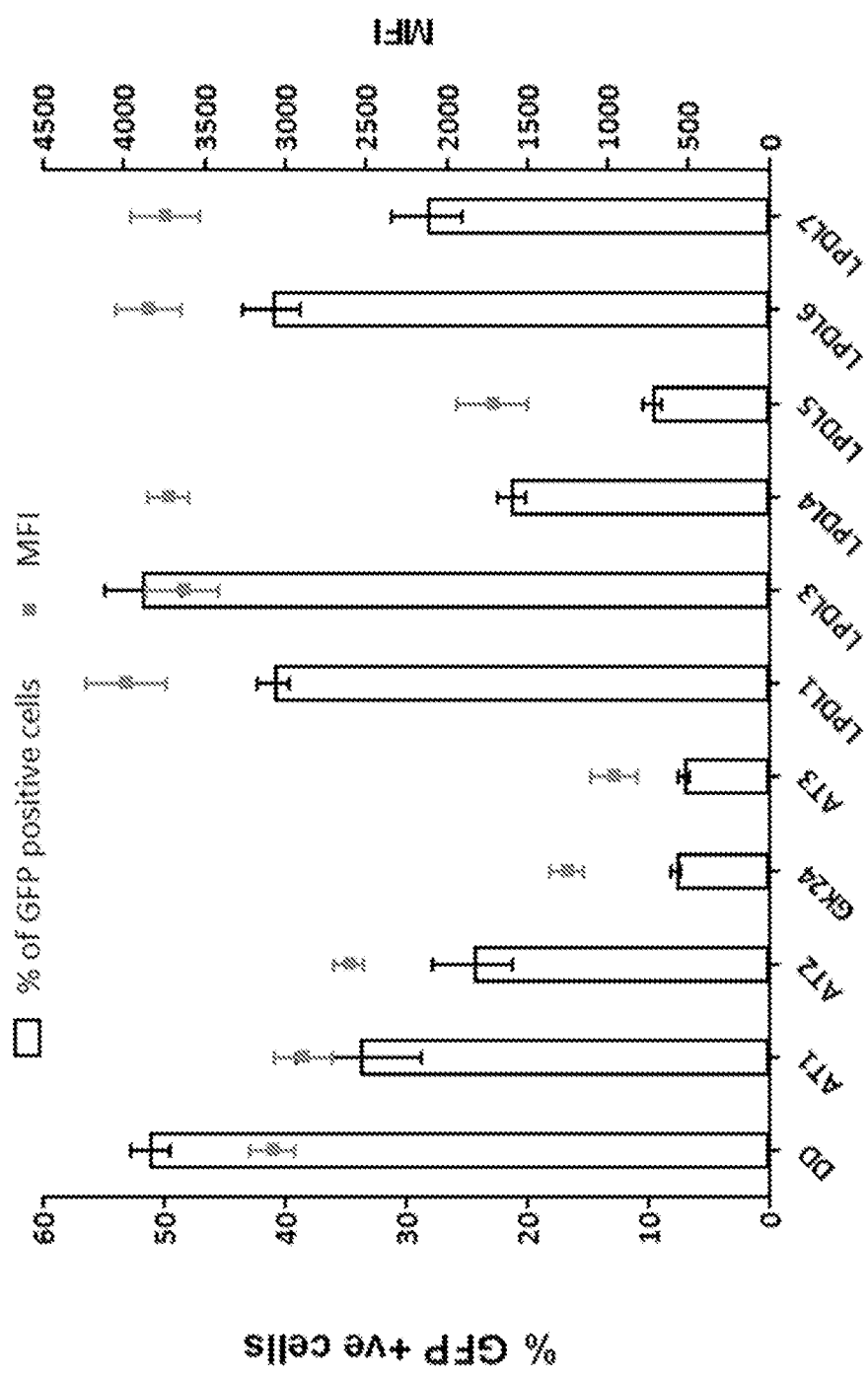
FIG. 13 shows flow cytometry data of the same cell transfections as shown in the images of FIG. 12.

ME27 cell lines were transfected with a GFP-reporter nucleic acid construct (pEGFP from Clontech™ under a CMV promoter) using complexes of the prior art or of the invention. Constructs used are "D-D" (DOTMA/DOPE), AT1 and LPDL1 to LPDL6 of each pair in FIG. 12 shows a phase contrast view of the cells and the second photograph shows the fluorescence of the cells. The number of fluorescent cells and their fluorescence intensity (mean fluorescence intensity was quantified and is shown in FIG. 13). This shows that the percentage of positive cells was at least as high using the transfection complex of the invention as compared to those of the prior art and, with the exception of the "LPDL5" replicate the fluorescence intensity was higher for complexes of the invention. FIG. 13 shows flow cytometry data from the same transfections shown in FIG. 12.

Example 10—Intravenous Targeting of Tumours

NSG-mice that were engrafted with Kelly cells were used as xenograft models. The read-out was if the complexes selectively targeted the tumour cells. The tumours were targeted with the anionic complexes (RTNs) of the invention or for comparison cationic prior art complexes. The complexes containing the integrin-targeting peptide ME27 and the cationic formulation contained Lipid DOTMA/DOPE and 1% PEG2000 (i.e. AT1): peptide ME27: siRNA labelled with dy677; the anionic formulation contained a core of DOTMA/DOPE: peptide ME27: siRNA labelled with dy677 and then on the outer layer had anionic lipid.

Figure 14A:
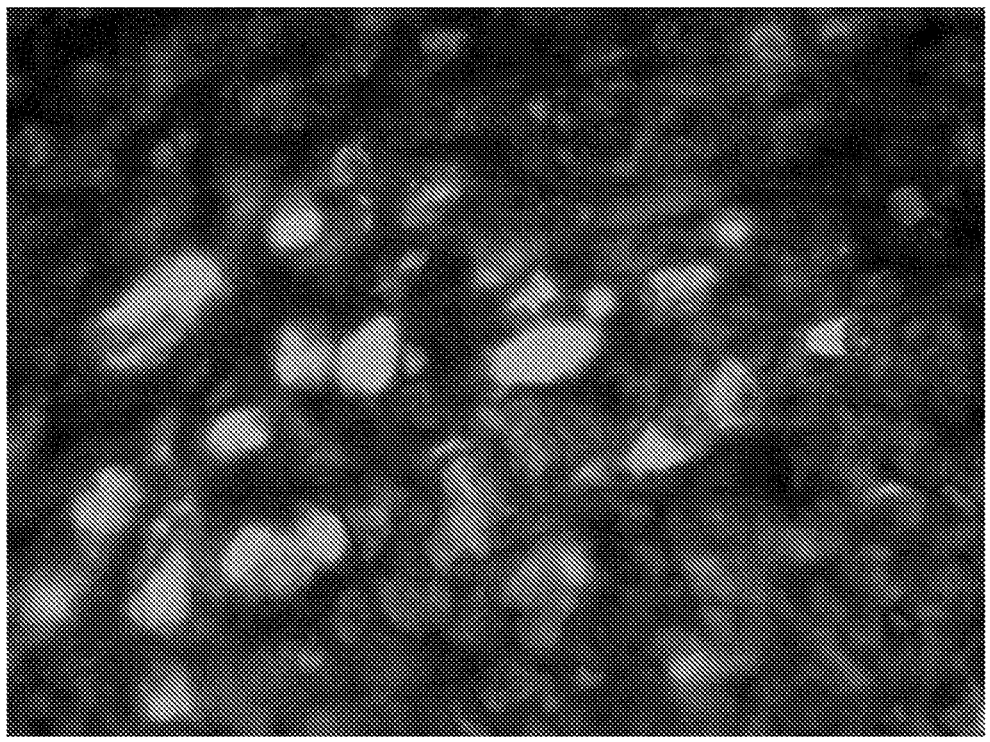
FIG. 14 shows photographs of cells from tumour-bearing mice illustrating that nanoparticles of the invention can be used to target the cells.
Figure 14B:
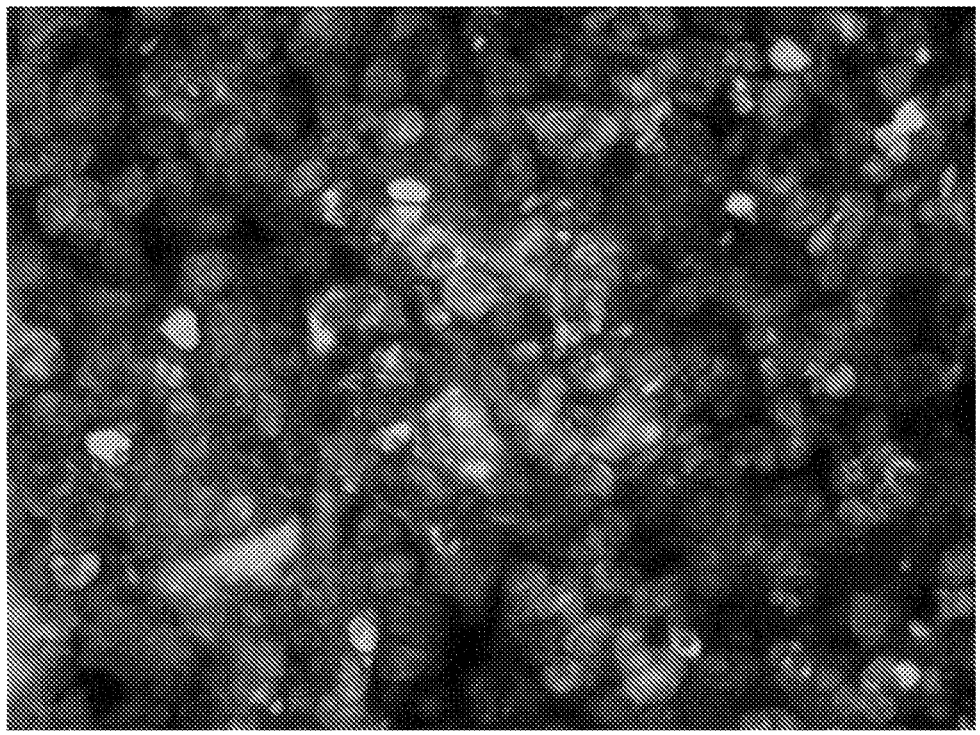

FIG. 14 shows (in green in the original) targeted transfection of the Kelly cells.

Example 11—Flow Cytometric Analysis of Transfection Efficiency

Figure 15A:
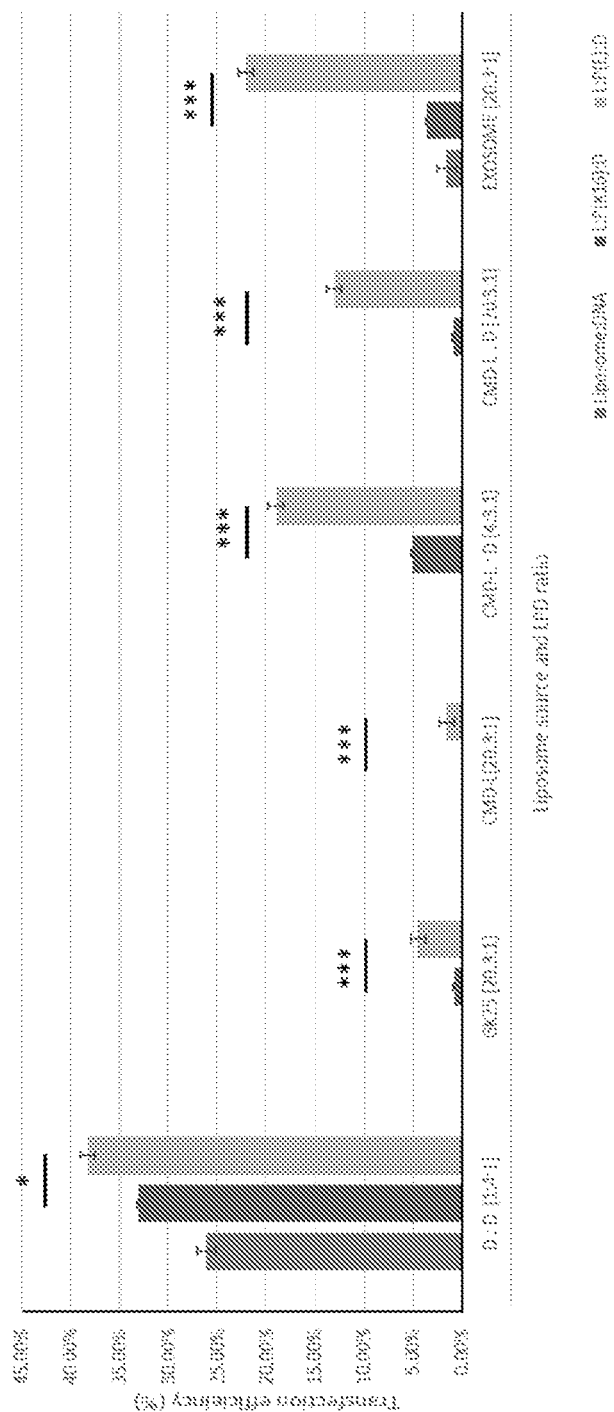
FIG. 15 shows flow cytometry data comparing the specificity of different nanoparticles in a) N2A cells, b) H441 cells, or c) 16-HBE cells.
Figure 15B:
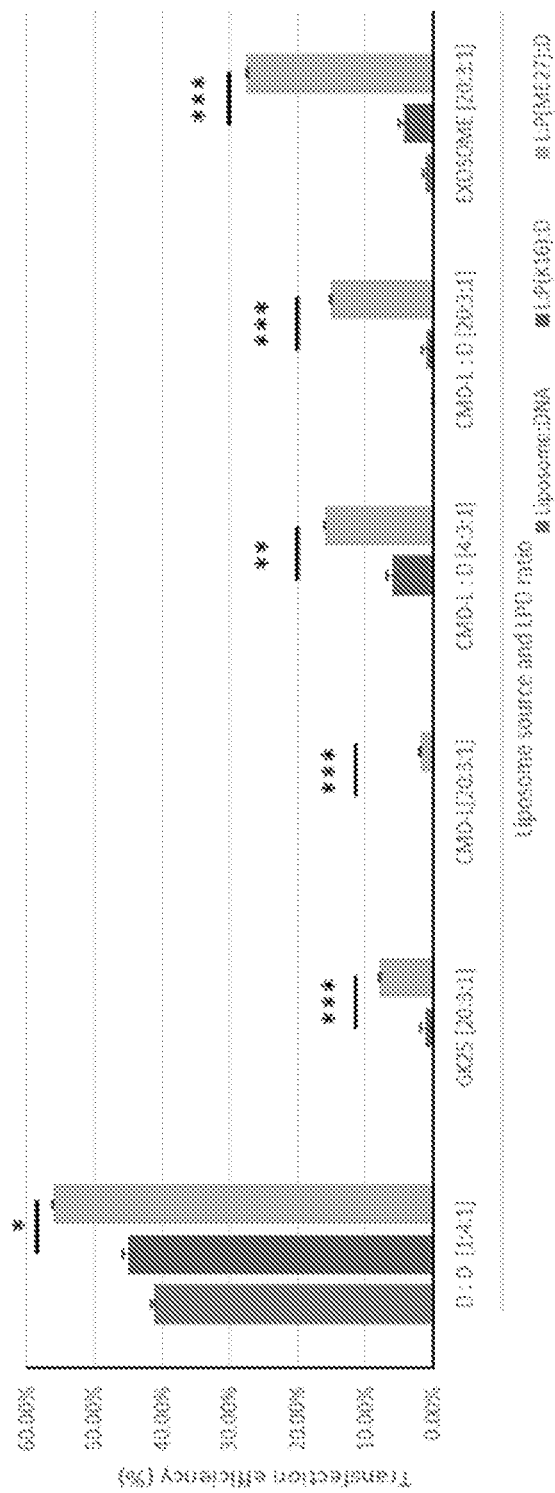
Figure 15C:
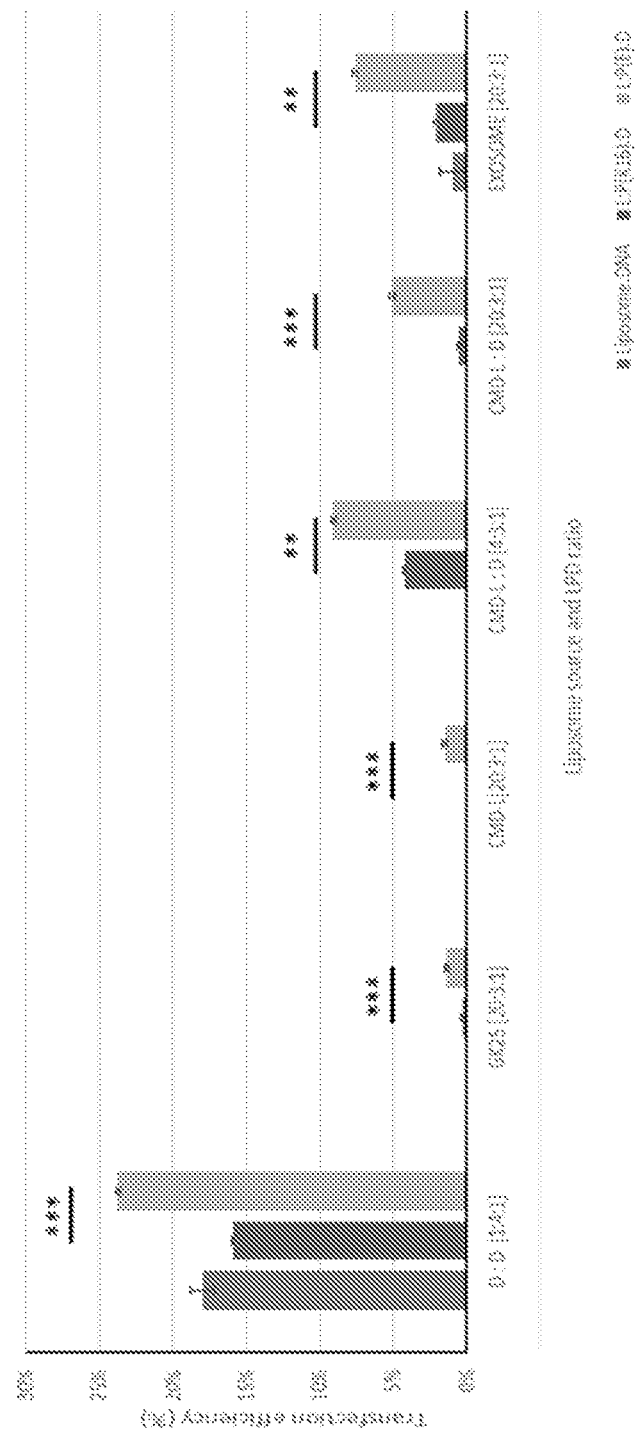

The specificity of each nanocomplex was measured by comparing transfection efficiencies of targeting and non-targeting nanocomplexes in 3 cell lines. FIG. 15 panel A shows the Flow cytometry data for N2a. Overall D:D had the highest overall efficiency compared to the other nanocomplexes, however it was also the least specific as its non-targeting complex transfected over 45%. The transfection efficiencies for all the other anionic or exosome containing nanocomplexes was greatly enhanced by the targeting moiety. Panel B shows similar results for the H441 cell line. For D:D however the presence of the targeting peptide was more significant than in N2a. In fact the lipoplex performed better than the non-targeting complex. Exosomes which had the second highest transfection efficiency in N2a were slightly less efficient than the cationic cmd-L:D, the targeting peptide was slightly less significant in H441 with exosomes. Panel C shows the flow cytometry data for 16-HBE cells.

The results mirror those of N2a, D:D was again the highest transfecting and least specific with the exosomes showing the second highest transfection efficiency. In all three cell lines anionic nanocomplexes had a higher specificity than the cationic nanocomplexes. Of the anionic liposomes, the exosomes showed the least specificity in all cell lines.

FIG. 15 Flow cytometry data comparing the specificity of the different nanocomplexes in A) N2a cells B) H441 cells and C) 16-HBE cells. The results show the comparison between liposome: DNA complexes, non-targeting complexes, and targeting complexes. D.D (DOTMA: DOPE), CMD-L (cell membrane derived—liposome), CMD-L:D (cell membrane derived-liposome:DOPE). (±St. Deviation, n=3). Probability values p≤0.05, p≤0.01, and p≤0.001 were assigned as *, , and *, respectively.

The invention claimed is:

1. A non-viral delivery complex, comprising:
   A, a cationic core which is a nanoparticle comprising:
   (i) a peptide of formula A-B—C wherein A is a polycationic nucleic acid binding component, B is a spacer element that is susceptible to cleavage within a cell, and C is a cell surface receptor binding component,
   (ii) a nucleic acid, and
   (iii) a cationic lipid; and
   B, an anionic coating which is a liposome surrounding the cationic core and which comprises lipids previously extracted from a plasma membrane of a subject's cells or exosomes or derivatives thereof.

2. The non-viral delivery complex according to claim 1, wherein at least 80% by weight of the anionic coating have been previously extracted from plasma membrane of the subject's cells or exosomes.

3. The non-viral delivery complex according to claim 1, wherein the anionic coating comprises PEGylated lipids.

4. The non-viral delivery complex according to claim 1, wherein the anionic coating comprises at least 80% by weight which has been extracted from the subject's cells or exosomes and wherein at least 1% by weight consists of PEGylated lipids.

5. The non-viral delivery complex according to claim 3 wherein the PEGylated lipids are lipids previously extracted from a plasma membrane of the subject's cells or exosomes which have been subsequently derivatized with PEG.

6. The non-viral delivery complex according to claim 1, wherein the nucleic acid is a small interfering RNA which down-regulates the expression of a gene which is differentially upregulated in tumour cells.

7. The non-viral delivery complex according to claim, 1, wherein the nucleic acid encodes the cystic fibrosis transmembrane conductance regulator.

8. The non-viral delivery complex according to claim 1 wherein the cell surface binding component binds to lung epithelial cells.

9. The non-viral delivery complex according to claim 1 wherein the ratio of cationic core A to anionic coating B is between 5 and 30.

10. A pharmaceutical composition for treating a subject which comprises the non-viral delivery complex in accordance with claim 1 in admixture or conjunction with a pharmaceutically suitable carrier.

11. A method of making a non-viral delivery complex, comprising:
    A, making a cationic core which is a nanoparticle comprising: (i) a peptide of formula A-B—C wherein A is a polycationic nucleic acid binding component, B is a spacer element that is susceptible to cleavage within a cell, and C is a cell surface receptor binding component, (ii) a nucleic acid, and optionally (iii) a cationic lipid, and
    B, adding an anionic coating which is a liposome surrounding the cationic core and which comprises lipids previously extracted from a plasma membrane of the subject's cells or exosomes or derivatives thereof.

12. A method for the treatment of a condition caused in a subject by a defect and/or a deficiency in a gene or for immunisation, or for anti-sense or RNAi therapy, which comprises administering a non-viral delivery complex of claim 1 to the subject.

13. A method for the treatment of a subject suffering from a cancer which comprises administering a non-viral delivery complex of claim 1 to the subject.

14. A method for the treatment of a subject suffering from a cystic fibrosis which comprises administering a non-viral delivery complex of claim 7 to the subject.

15. A pharmaceutical composition comprising a non-viral delivery complex of claim 1.

16. The non-viral delivery complex of claim 1, wherein the lipids comprise lipids derived from the subject's red blood cells.

* * * * *